US012653605B2

(12) United States Patent
DiCicco et al.

(10) Patent No.: US 12,653,605 B2
(45) Date of Patent: Jun. 16, 2026

(54) TREATMENT TIME DURATION IDENTIFIED IN ELECTROCARDIOGRAM TRACING

(71) Applicant: Boston Scientific Medical Device Limited, Galway (IE)

(72) Inventors: Matthew DiCicco, Mississauga (CA); Kaylie Lau, Mississauga (CA)

(73) Assignee: Boston Scientific Medical Device Limited, Galway (IE)

( * ) Notice: Subject to any disclaimer, the term of this patent is extended or adjusted under 35 U.S.C. 154(b) by 325 days.

(21) Appl. No.: 18/681,411

(22) PCT Filed: Jul. 27, 2022

(86) PCT No.: PCT/IB2022/056950
§ 371 (c)(1),
(2) Date: Feb. 5, 2024

(87) PCT Pub. No.: WO2023/012608
PCT Pub. Date: Feb. 9, 2023

(65) Prior Publication Data
US 2024/0307106 A1     Sep. 19, 2024

Related U.S. Application Data

(60) Provisional application No. 63/229,572, filed on Aug. 5, 2021.

(51) Int. Cl.
*A61B 18/14*          (2006.01)
*A61B 18/00*          (2006.01)
*A61B 18/12*          (2006.01)

(52) U.S. Cl.
CPC ...... *A61B 18/1477* (2013.01); *A61B 18/1206* (2013.01); *A61B 2018/00351* (2013.01);
(Continued)

(58) Field of Classification Search
CPC ............ A61B 18/1477; A61B 18/1206; A61B 2018/00351; A61B 2018/00577;
(Continued)

(56) References Cited

U.S. PATENT DOCUMENTS

| | | |
|---|---|---|
| 2008/0249425 A1 | 10/2008 | Phillips |
| 2015/0094604 A1 | 4/2015 | Amann |

(Continued)

FOREIGN PATENT DOCUMENTS

| | | |
|---|---|---|
| CN | 106539580 A | 3/2017 |
| CN | 110680302 A | 1/2020 |

OTHER PUBLICATIONS

International Search Report and Written Opinion received for PCT Patent Application No. PCT/IB2022/056950, mailed on Oct. 17, 2022, 11 pages.

(Continued)

*Primary Examiner* — Linda C Dvorak
*Assistant Examiner* — Abigail Bock
(74) *Attorney, Agent, or Firm* — Nelson Mullins Riley & Scarborough LLP

(57)          ABSTRACT

Computer system is configured to receive electrocardiogram signal, from electrocardiographic sensor, configured to indicate cardiac cycle of heart of patient. Computer system is also configured to generate electrocardiogram tracing based on electrocardiogram signal that was received. Computer system is also configured to identify treatment time duration is configured to span a part of electrocardiogram tracing that was generated, and tissue layer is treatable during, at least in part, treatment time duration. This is done in such a way that, during treatment time duration, blood pressure within heart urges tissue layer to impart relatively lower amount of tissue force toward treatment device while treatment device is positioned proximate to tissue layer, and treatment device is (Continued)

activated to treat the tissue layer. The computer system is also configured to provide treatment time duration that was identified.

20 Claims, 16 Drawing Sheets

(52) U.S. Cl.
    CPC ............... *A61B 2018/00577* (2013.01); *A61B 2018/00642* (2013.01); *A61B 2018/00708* (2013.01); *A61B 2018/00761* (2013.01); *A61B 2018/00839* (2013.01); *A61B 2018/1425* (2013.01)

(58) Field of Classification Search
    CPC   A61B 2018/00642; A61B 2018/00708; A61B 2018/00761; A61B 2018/00839; A61B 2018/1425
    See application file for complete search history.

(56)                  References Cited

U.S. PATENT DOCUMENTS

2017/0258521  A1      9/2017   Asirvatham et al.
2019/0365268  A1     12/2019   Li

OTHER PUBLICATIONS

International Search Report for PCT Application No. PCT/IB2022/056950 mailed Oct. 17, 2022. 2 pages.

1

TREATMENT TIME DURATION IDENTIFIED IN ELECTROCARDIOGRAM TRACING

The present application is a national stage of International Application No. PCT/IB2022/056950, filed Jul. 27, 2022, which claims the benefit of U.S. Provisional Application No. 63/229,572, filed Aug. 5, 2021, the disclosure of which is incorporated herein in its entirety.

TECHNICAL FIELD

This document relates to the technical field of (and is not limited to): (A) an apparatus and/or method for use with an electrocardiogram signal configured to indicate (provide) a cardiac cycle of the heart (of a patient) having a tissue layer (of a patient) that is treatable by a treatment device; and/or (B) an apparatus and/or method for use with an electrocardiogram signal configured to indicate (provide) a cardiac cycle of the heart (of a patient) having the pericardium layer that is puncturable by a puncture device.

BACKGROUND

Known medical devices are configured to facilitate a medical procedure, and help healthcare providers diagnose and/or treat medical conditions of sick patients.

SUMMARY

It will be appreciated that there exists a need to mitigate (at least in part) at least one problem associated with known medical devices, such as treatment devices, puncture devices, etc. (also called the existing technology). After much studying and experimenting with the known medical devices, an understanding (at least in part) of the problem and its solution have been identified (at least in part) and are articulated (at least in part) as follows:

The pericardium may be called the pericardium layer, the pericardial layer, the pericardial sac, a tissue layer, etc. For instance, the pericardium layer is a membrane that directly surrounds the heart and defines the pericardial cavity. More specifically, the pericardium layer is a double-walled sac containing the heart and the roots of the major vessels (or other areas of proximity to the heart). The pericardial sac has two layers: a serous layer and a fibrous layer. The pericardial sac encloses the pericardial cavity which contains the pericardial fluid. The pericardial fluid is contained between the pericardial sac and the outer wall of the heart. The pericardial space (pericardial cavity) is the fluid-filled space between the parietal and visceral layers of the serous pericardium (in normal conditions, the pericardial space contains a small amount of serous pericardial fluid). The pericardium layer protects and lubricates the heart and keeps the heart in place within the chest. The pericardium layer includes two distinct sublayers: the sturdy outer fibrous pericardium and the inner serous pericardium. The fibrous pericardium is made of tough, dense connective tissue that protects the heart and maintains its position in the thorax. The more delicate serous pericardium includes two layers: (A) the parietal pericardium (which is fused to the fibrous pericardium), and (B) an inner visceral pericardium (which is fused to the heart and is part of the heart wall). The pericardial cavity (also called the pericardial space, which is filled with the pericardial fluid or a lubricating serous fluid) lies between the epicardium and the pericardium. The pericardial fluid acts as a lubricant to allow normal heart movement within the chest.

A medical-treatment procedure may include, for instance, epicardial access procedures, which come with an adverse medical complication rate that may range from between about five percent to about fifteen percent. The epicardial access procedures may result in adverse medical complications that may include, for instance, hemopericardium (that may further include or lead to cardiac tamponade), hemoperitoneum, injury to coronary vessels and/or a laceration (a deep cut or tear in flesh), etc. Hemopericardium is an adverse medical condition in which blood seeps into the pericardial sac of the heart, and it is clinically similar to a pericardial effusion, and, depending on the volume (of blood flow) and rapidity with which this condition develops, may cause cardiac tamponade. Cardiac tamponade is a serious adverse medical condition in which blood or fluids fill the space between the sac that encases the heart and the heart muscle, and places extreme pressure on the heart. Pressure prevents the ventricles (of the heart) from expanding fully and keeps the heart from functioning properly. A ventricle is one of two large chambers toward the bottom of the heart that collect and expel blood received from the atrium towards the peripheral beds within the body and lungs. The atrium (an adjacent/upper heart chamber that is smaller than a ventricle) primes the pump. Hemoperitoneum (haemoperitoneum, hematoperitoneum) is an adverse medical condition in which blood seeps into the peritoneal cavity (that is, blood accumulates in the space between the inner lining of the abdominal wall and the internal abdominal organs). The peritoneal cavity is the space within the abdomen that contains the intestines, the stomach, and the liver (it is bound by thin membranes).

A method (a medical treatment method) that may be utilized to gain access to the pericardial space is through percutaneous advancement (that is, access through the skin of the patient) of a medical treatment device (such as, a medical needle, a puncture device, etc.). For instance, the medical needle (medical treatment device) is moved toward the heart for the purpose of tenting the pericardium layer of the heart. After the pericardium layer is tented by the medical needle, the medical needle is further moved (advanced) to puncture (medically treat, mechanically puncture, emit energy or radio-frequency energy, for formation of a puncture, etc.) the pericardium layer of the heart. Unfortunately, adverse medical complications may arise from accidentally (unintentionally) advancing (moving) the puncture device beyond the pericardial space into an adjacently located tissue thereby imparting unwanted damage to the adjacently located tissue (the tissue located adjacent to the tissue receiving treatment). This unfortunate scenario may occur as a result of application of the treatment to the tissue at an undesirable time, such as when the blood pressure within the heart is increasing while the treatment device or puncture device is activated or utilized. The outer wall of the heart expands while, at the same time, the puncture device (positioned on the outer wall of the heart) is activated or used to form a puncture through the pericardium layer of the heart.

During a medical procedure, it may be possible (for a physician) to feel (that is, perceptible by touch via the puncture device, a medical treatment device, etc.) the heart palpitations imparted to (against) a distal tip portion of the puncture device (while the puncture device is manipulated, by the physician, to tent the pericardium layer of the heart). The action of tenting includes application of a temporary force to the pericardium layer in such a way that the pericardium layer forms a tent-like structure. This is done in preparation for (prior to) the formation of a puncture to be extended through the pericardium layer. Following the formation of the puncture, the distal tip portion (of the puncture device) is moved into the pericardial space (the pericardial sac of the heart). The physician applies a movement force to the distal tip portion (of the puncture device) toward the pericardium layer of the heart, and the distal tip portion impinges against the pericardium layer, and causing the distal tip to tent the pericardium layer. While the physician continues to apply the movement force to the distal tip portion (of the puncture device), the pericardium layer temporarily forms a tent structure, and the physician may sense (that is, perceptible by touch, or tactilely, via the puncture device) the palpitations of the heart (via the handling of the puncture device) which are applied as an opposite force (tissue force or heart-beat force) against the tented pericardium layer of the heart. Under this condition, disadvantageously, the palpitations of the heart may (inadvertently) urge the distal tip portion (of the puncture device) to inadvertently advance (move) through the pericardium layer into the pericardial space (sac) of the heart (thereby, disadvantageously puncturing the pericardium layer at an undesirable or unexpected time), which may lead to a potential adverse medical condition (situation) (unwanted damage to tissue that is not to be treated, such as the heart muscle of the patient).

As the physician may tactilely detect (sense, feel) heart palpitations impinging against the puncture device (while the puncture device tents the pericardium layer), the tissue force of the heart palpitations may result in inadvertent puncturing through the pericardial sac (the pericardium layer) and into the pericardial space (the space immediately below the inner surface of the pericardium layer).

There may exist an opportunity to control or adjust the amount (and/or duration of) the emission of radio-frequency energy (used for puncturing the pericardium layer) during an advantageous time interval (time duration) in which there may be a reduction (preferably elimination) of unintended adverse medical complications while the pericardium layer is punctured by the puncture device.

The cardiac cycle is a sequence of events in a single heartbeat. The systole phase (also referred to as systole) is a period of contraction of the ventricles of the heart that occurs between the first and second heart sounds of the cardiac cycle. Systole causes the ejection of blood into the aorta and pulmonary trunk. During the systole phase, the heart enters isovolumetric contraction in which the heart pumps out, on average, about sixty percent of its blood volume causing displacement of heart tissue within the pericardial sac. The RR-interval is the time (time duration) between neighboring heartbeats. The beginning of the RR-interval is marked by the left ventricular end-diastolic volume (the peak blood volume), which then declines during about 0.4 seconds to the left ventricular end systolic volume (the minimum blood volume). The end systolic volume (ESV) is the volume of blood in the ventricle at the end of contraction (or the systole phase), and the beginning of filling (or diastole). The end systolic volume is the lowest volume of blood in the ventricle at any point in the cardiac cycle. The main factors that affect the end systolic volume are afterload and the contractility of the heart. Afterload is the pressure that the heart must work against to eject blood during systole (ventricular contraction). Afterload is proportional to the average arterial pressure. For instance, it may be desirable to puncture the pericardium of the heart by applying or emitting energy to the pericardium during the RR-interval (preferably, emitting energy at the start of the RR-interval and stopping emission of energy before the end of the RR-interval). The energy may be emitted as radio-frequency energy from a radio-frequency emitting puncture device, etc. It will be appreciated that reducing force on the distal tip during the emission of energy may reduce the depth of tissue punctured and, in turn, reduce the risk of puncturing myocardial tissue (which is located adjacent to the pericardium layer). Timing the emission or delivery of the energy to a set time (also called, a predetermined time duration) may result in an acceptable time (for the physician) to apply a movement force to a puncturing device (preferably, to a distal tip thereof) while energy is emitted, preferably without inadvertently imparting damage to the tissue (which is not to receive treatment) located adjacent to the pericardium layer (which is to receive treatment). It will be appreciated that the set time may span a part of (be identified in) the electrocardiogram signal that may be used for the formation (generation) of an electrocardiogram tracing.

It may be desirable to puncture the pericardium of the heart by applying (emitting) radio-frequency energy to the pericardium layer from a radio-frequency emitting puncture device. Preferably, the radio-frequency emitting puncture device is configured to sense or detect an electrocardiogram signal (also called an ECG signal or an EKG signal) at the distal tip of the radio-frequency emitting puncture device. The distal tip (of the radio-frequency emitting puncture device) is configured to detect (sense) the beginning of the RR-interval. The radio-frequency emitting puncture device is configured (preferably) to apply or emit a pulse of radio-frequency energy (the pulse having a duration of about 0.1 seconds to about 0.4 seconds) to the pericardium during the RR-interval (to be derived from the electrocardiogram tracing that was computed or generated based on the electrocardiogram signal associated with the heartbeat of the heart). The RR-interval is detected (preferably) by the radio-frequency emitting puncture device (for convenience). The pulse of radio-frequency energy (to be emitted by the radio-frequency emitting puncture device) is sufficient enough to facilitate puncturing, without inadvertently causing damage to the tissue located proximate to the pericardium of the heart (during the RR-interval).

It will be appreciated that the application (emission) of energy (from the puncture device) may be activated during other (suitable) time intervals, or treatment time durations, and these time intervals are to be derived from the electrocardiogram tracing (or any equivalent thereof) that was computed, or generated, based on the electrocardiogram signal (of the heartbeat of the heart). In this arrangement, puncturing (treatment) is facilitated (accommodated) while lowering the possibility of unwanted damage (or reducing inadvertently causing damage) to adjacently positioned tissue that is not to receive treatment (such as, the tissues of the heart not to be treated or punctured, etc.).

It will be appreciated that the application (emission) of energy (radio-frequency energy) is to remain deactivated during other (suitable) intervals (to thereby avoid inadvertent or unwanted damage to the heart or other tissue, which are not to receive treatment and/or puncture).

For instance, it may be desirable to utilize a radio-frequency puncturing device configured to detect (record) electrocardiographic information, electrocardiogram tracing, or any equivalent thereof. The electrocardiogram tracing is obtained from an electrocardiogram signal emitted from an electrocardiogram sensor positioned at the distal tip of the puncture device, etc., or any equivalent thereof. The puncturing device may also be configured to provide feedback to the user for puncture timing. The radio-frequency puncturing device may also be configured to provide a time-duration limit (a limit setting) so that radio-frequency energy may only be applied during the time-duration limit (a set time period or a desired treatment time duration). The radio-frequency puncturing device may also be configured to use the electrocardiogram signal to distinguish between the systole phase and the diastole phase of the heart, such as: (A) isovolumetric contraction (IC), (B) ejection, (C) isovolumetric relaxation (IR), (D) rapid inflow, (E) diastasis, and/or (F) atrial systole, etc. It will be appreciated that, for instance, the beginning of the RR-interval marks the maximum amplitude generally seen in the electrocardiogram signal, and, therefore, it may be easier to detect the beginning of isovolumetric contraction (IC) with a larger degree of confidence than for other phases.

To mitigate, at least in part, at least one problem associated with the existing technology, there is provided (in accordance with a major aspect) an apparatus. The apparatus is for use with an electrocardiogram signal. The electrocardiogram signal is configured to indicate (provide) a cardiac cycle of the heart, of a patient. The patient has a tissue layer that is treatable by a treatment device. The apparatus includes (comprises) a computer system configured to receive the electrocardiogram signal, from an electrocardiographic sensor, configured to indicate (provide) the cardiac cycle of the heart. The computer system is also configured to generate an electrocardiogram tracing based on the electrocardiogram signal that was received. The computer system is also configured to identify a treatment time duration. The treatment time duration may include a puncture time duration, etc. and any equivalent thereof, and is configured to span a part of the electrocardiogram tracing that was generated. The tissue layer is treatable during, at least in part, the treatment time duration. This is done in such a way that, during, at least in part, the treatment time duration, the blood pressure within the heart urges the tissue layer to impart a relatively lower amount of tissue force toward the treatment device while (A) the treatment device is positioned proximate to the tissue layer, and (B) the treatment device is activated to treat the tissue layer. The computer system is also configured to provide the treatment time duration that was identified.

To mitigate, at least in part, at least one problem associated with the existing technology, there is provided (in accordance with a major aspect) an apparatus. The apparatus is for use with an electrocardiogram signal configured to indicate (provide) a cardiac cycle of the heart of a patient, the patient having the pericardium layer of the heart, the pericardium layer being puncturable by (to be punctured by) a puncture device. The apparatus includes (comprises) a computer system configured to receive the electrocardiogram signal, from an electrocardiographic sensor. The electrocardiogram signal is configured to indicate (provide) the cardiac cycle of the heart having the pericardium layer to be punctured by the puncture device. The computer system is also configured to generate an electrocardiogram tracing based on the electrocardiogram signal that was received. The computer system is also configured to identify a treatment time duration. The treatment time duration is configured to span a part of the electrocardiogram tracing that was generated. The pericardium layer is puncturable during, at least in part, the treatment time duration. This is done in such a way that inadvertent damage to the tissue (located adjacent to the pericardium layer) is reduced (preferably avoided) while the pericardium layer is punctured during the treatment time duration. The computer system (preferably) is also configured to identify a treatment time duration. The treatment time duration is configured to span a part of the electrocardiogram tracing that was generated. The pericardium layer is puncturable during, at least in part, the treatment time duration. This is done in such a way that, during, at least in part, the treatment time duration, the blood pressure within the heart urges the pericardium layer to impart a relatively lower amount of tissue force toward the puncture device while the puncture device is positioned proximate to the pericardium layer. The puncture device is activated to puncture the pericardium layer. The computer system is also configured to provide (write, output, transmit) the treatment time duration that was identified.

Other aspects are identified in the claims. Other aspects and features of the non-limiting embodiments may now become apparent to those skilled in the art upon review of the following detailed description of the non-limiting embodiments with the accompanying drawings. This Summary is provided to introduce concepts in simplified form that are further described below in the Detailed Description. This Summary is not intended to identify potentially key features or possible essential features of the disclosed subject matter, and is not intended to describe each disclosed embodiment or every implementation of the disclosed subject matter. Many other novel advantages, features, and relationships will become apparent as this description proceeds. The figures and the description that follow more particularly exemplify illustrative embodiments.

BRIEF DESCRIPTION OF THE DRAWINGS

The non-limiting embodiments may be more fully appreciated by reference to the following detailed description of the non-limiting embodiments when taken in conjunction with the accompanying drawings, in which.

Figure 1:
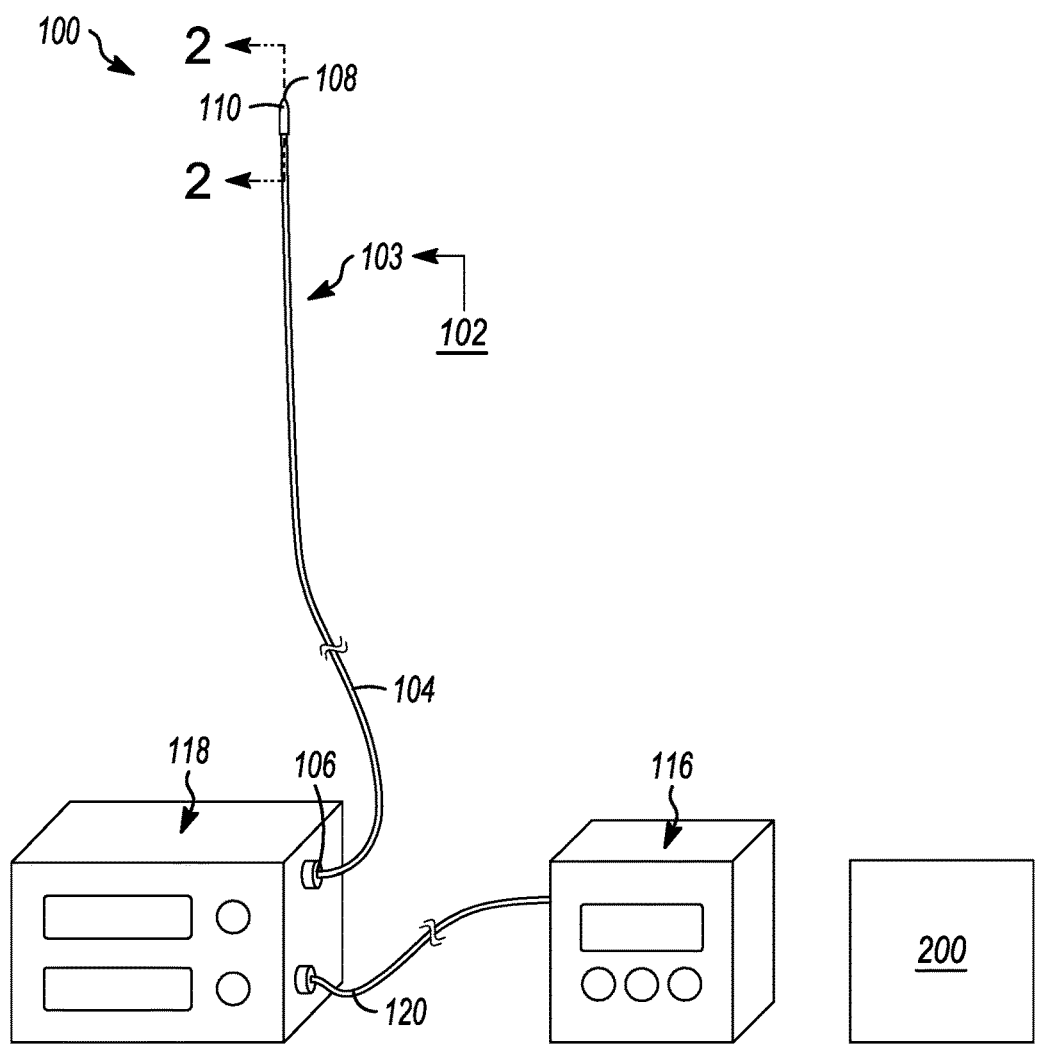
FIG. 1 and FIG. 2 depict a side view (FIG. 1) and a cross-sectional view (FIG. 2) of embodiments of a puncture device.

The drawings are not necessarily to scale and may be illustrated by phantom lines, diagrammatic representations and fragmentary views. In certain instances, details unnecessary for an understanding of the embodiments (and/or details that render other details difficult to perceive) may have been omitted. Corresponding reference characters indicate corresponding components throughout the several figures of the drawings. Elements in the several figures are illustrated for simplicity and clarity and have not been drawn to scale. The dimensions of some of the elements in the figures may be emphasized relative to other elements for facilitating an understanding of the various disclosed embodiments. In addition, common, and well-understood, elements that are useful in commercially feasible embodiments are often not depicted to provide a less obstructed view of the embodiments of the present disclosure.

DETAILED DESCRIPTION OF THE NON-LIMITING EMBODIMENT(S)

The following detailed description is merely exemplary and is not intended to limit the described embodiments or the application and uses of the described embodiments. As used, the word "exemplary" or "illustrative" means "serving as an example, instance, or illustration." Any implementation described as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure. The scope of the disclosure is defined by the claims. For the description, the terms "upper," "lower," "left," "rear," "right," "front," "vertical," "horizontal," and derivatives thereof shall relate to the examples as oriented in the drawings. There is no intention to be bound by any expressed or implied theory in the preceding Technical Field, Background, Summary or the following detailed description. It is also to be understood that the devices and processes illustrated in the attached drawings, and described in the following specification, are exemplary embodiments (examples), aspects and/or concepts defined in the appended claims. Hence, dimensions and other physical characteristics relating to the embodiments disclosed are not to be considered as limiting, unless the claims expressly state otherwise. It is understood that the phrase "at least one" is equivalent to "a". The aspects (examples, alterations, modifications, options, variations, embodiments and any equivalent thereof) are described regarding the drawings. It should be understood that the disclosure is limited to the subject matter provided by the claims, and that the disclosure is not limited to the particular aspects depicted and described. It will be appreciated that the scope of the meaning of a device configured to be coupled to an item (that is, to be connected to, to interact with the item, etc.) is to be interpreted as the device being configured to be coupled to the item, either directly or indirectly. Therefore, "configured to" may include the meaning "either directly or indirectly" unless specifically stated otherwise.

Figure 2:
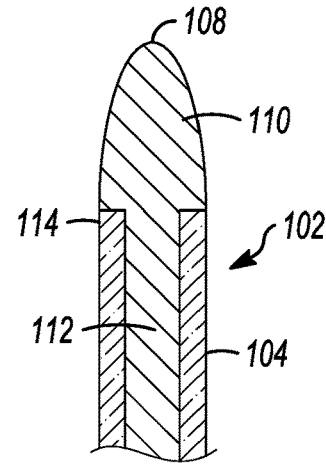

FIG. 1 and FIG. 2 depict a side view (FIG. 1) and a cross-sectional view (FIG. 2, in which the view is taken along line 2-2 in FIG. 1) of embodiments of a puncture device 102.

Referring to the embodiment as depicted in FIG. 1, a system 100 includes a puncture device 102. The puncture device 102 is configured to be positioned proximate to the tissue of the patient (such as, the pericardium of the heart). The puncture device 102 is also configured to advance across (through) the tissue (preferably, without requiring the application of an excessive movement force to the puncture device 102). The puncture device 102 is (preferably) configured to emit (selectively emit) energy toward the tissue (after the puncture device 102 is positioned proximate to the tissue). The energy (once activated to be emitted from the puncture device 102) is utilized (at least in part) for puncturing the tissue, etc. For instance, the puncture device 102 may include an energy-emitting puncture device 103. An embodiment of the energy-emitting puncture device 103 includes a radio-frequency emitter device, a radio-frequency probe, the NRG (TRADEMARK) RF TRANSSEPTAL needle (manufactured by BAYLIS MEDICAL, headquartered in Canada), and any equivalent thereof.

Referring to the embodiment as depicted in FIG. 1, the puncture device 102 includes biocompatible material properties configured for specific performances (such as, dielectric strength, thermal insulation, electrical insulation, corrosion resistance, water resistance, heat resistance, etc.) for compliance with industrial and/or regulatory safety standards (compatible for medical usage), etc. Reference is made to the following publication for consideration in the selection of suitable materials for the puncture device 102: Plastics in Medical Devices: Properties, Requirements, and Applications; 2nd Edition; author: Vinny R. Sastri; hardcover ISBN: 9781455732012; published: 21 Nov. 2013; publisher: Amsterdam [Pays-Bas]: Elsevier/William Andrew, [2014].

Referring to the embodiment as depicted in FIG. 1, the puncture device 102 may include (for instance) a shape-memory material configured to be manipulated and/or deformed followed by a return to the original shape that the shape-memory material was set in (prior to manipulation). Shape-memory materials (SMMs) are known and not further described in detail. Shape-memory materials are configured to recover their original shape from a significant and seemingly plastic deformation in response to a particular stimulus being applied to the shape-memory material. This is known as the shape memory effect (SME). Superelasticity (in alloys) may be observed once the shape-memory material is deformed under the presence (an application) of a stimulus force.

Referring to the embodiment as depicted in FIG. 1, the puncture device 102 is configured to be inserted into a confined space defined by a living body (the patient). The puncture device 102 includes (preferably) a relatively thin and flexible wire (an elongated flexible shaft) configured to be inserted into a confined or tortuous space (a confined space) defined by the living body (of the patient), either inserted by itself or with the cooperation of an introducer device (known and not depicted). The puncture device 102 is (preferably) impermeable by a bodily fluid located in the confined space defined by the living body.

Referring to the embodiment as depicted in FIG. 1, there is provided an apparatus for use with an electrocardiogram signal (to be provided by an electrocardiographic sensor, which is known and not depicted). The electrocardiogram signal is configured to indicate (provide) a cardiac cycle of the heart of a patient. The heart has tissue (such as, the pericardium layer) that is puncturable by (to be punctured by) a puncture device 102. This is done, preferably, by utilizing the emission of energy from the puncture device 102, and is not limited to the emission of energy. The apparatus includes a computer system 200 configured to receive (read, input) the electrocardiogram signal (from the electrocardiographic sensor, known and not depicted). The electrocardiogram signal is configured to indicate (provide) the cardiac cycle of the heart having the pericardium layer to be punctured by the puncture device 102. The computer system 200 is also configured to generate (compute, calculate) an electrocardiogram tracing 300 (as depicted in FIG. 5, FIG. 6, FIG. 7, and FIG. 10), and/or any equivalent thereof. The electrocardiogram tracing 300 is any tracing (a waveform) derived from any type of signal (electrical signal, acoustic signal, pressure signal, etc.) provided by any suitable transducer and/or sensor. The electrocardiogram tracing 300 is based on the electrocardiogram signal that was received (by the computer system 200). The computer system 200 is also configured to identify (compute, calculate) a treatment time duration (500, 600, 700, 1000) (as depicted in FIG. 5, FIG. 6, FIG. 7 and FIG. 10). The treatment time duration (500, 600, 700, 1000) is configured to span (spans) a part of (or as identifiable in) the electrocardiogram tracing 300 that was generated. The pericardium layer (of the heart) is puncturable by the puncture device 102, during, at least in part, the treatment time duration (500, 600, 700, 1000). This is done in such a way that inadvertent damage to the tissue (that is not to be treated or punctured, etc.) located adjacent to the pericardium layer is reduced (is preferably avoided) while the pericardium layer is punctured during the treatment time duration (500, 600, 700, 1000). The computer system 200 is also configured to provide (write, output, transmit) the treatment time duration (500, 600, 700, 1000) that was identified (computed), such as to the puncture device 102 and/or an auxiliary device (such as, a recording device). Advantageously, utilization of the computer system 200 may result in a relatively safer (a lower) amount of application force to be imparted to the tissue from the puncture device 102 when the tissue is punctured (by the puncture device 102); this is done, preferably, without causing or imparting inadvertent damage to any neighboring tissue (which is not to be punctured or treated). Therefore, the physician may be more confident that an optimal contact force might be achieved between the puncture device 102 and the pericardium layer before the pericardium layer is punctured.

Referring to the embodiment as depicted in FIG. 1, the computer system 200 includes a memory assembly (known and not depicted) configured to receive and tangibly store an executable program (known and not depicted). The executable program includes coded instructions (programmed coded instructions) configured to be readable by, and executable by, a processor (known and not depicted) of the computer system 200. The executable program is configured to urge the processor to perform predetermined controller operations of the computer system 200. Equivalents to the executable program include (and are not limited to): (A) machine-language code, (B) assembly-language code, (C) source code formed in a high-level computing language understood by humans (high-level language of the source code is compiled into either an executable machine code file or a non-executable machine-code object file), and/or (D) an application-specific integrated circuit and any equivalent thereof, and/or a field-programmable gate array (FPGA), or any equivalent thereof. It will be appreciated that the predetermined controller operations are part of a computing method, and may include an operating step of computing by using the processor (of the computer system 200) to provide (execute) computing functions and/or calculations (comparisons, etc.). Computing hardware and other operating components are utilized and are suitable for performing the computing processes of the embodiments and are not intended to limit the applicable environments. A person skilled in the art will immediately appreciate that the embodiments may be practiced with other computer system configurations, including set-top boxes, hand-held devices, multiprocessor systems, microprocessor-based or programmable consumer electronics, network computers, minicomputers, mainframe computers, and the like. The processor (of the computer system 200) may include a conventional microprocessor such as the INTEL (TRADEMARK) PENTIUM (TRADEMARK) microprocessor, manufactured by INTEL (TRADEMARK) based in the U.S.A., or the MOTOROLA (TRADEMARK) POWER PC (TRADEMARK) microprocessor (manufactured by MOTOROLA based in the U.S.A.), etc. A person of skill in the art will immediately recognize that the term memory assembly (also called a computer-readable medium or a machine-readable medium, etc.) may include any type of storage device that is accessible by the processor of the computer system 200 or by other equivalent data processing systems. The memory assembly may be embodied on a magnetic hard disk or an optical disk having executable instructions to cause the processor assembly to perform a computing method (operational steps or computing operations, etc.). Computer hardware (operating components and any equivalent thereof and suitable for performing the processes of the embodiments) is not intended to limit the applicable environments. The computer system 200 may include a processor, and a non-transitory computer-readable storage medium including computer-executable instructions that are executable by the processor in such a way that the processor is urged to perform operations (as identified in other paragraphs). A computer-implemented method is a method that, when executed by the processor of the computer system 200 computer, causes the processor to perform operations.

Referring to the embodiment as depicted in FIG. 1, there is provided an apparatus for use with an electrocardiogram signal configured to indicate (provide) a cardiac cycle of the heart of a patient. The patient has a tissue layer (such as, the pericardium layer of the heart) that is treatable (such as, is puncturable) by a treatment device (such as, a puncture device 102). The apparatus includes a computer system 200 configured to receive (read, input) the electrocardiogram signal (from an electrocardiographic sensor). The electrocardiogram signal is configured to indicate (provide) the cardiac cycle of the heart. The computer system 200 is also configured to generate (compute, calculate) an electrocardiogram tracing 300 based on the electrocardiogram signal that was received. The computer system 200 is also configured to identify (compute, calculate) a treatment time duration (500, 600, 700, 1000), also called a treatment time duration (as depicted in FIG. 5, FIG. 6, FIG. 7 or FIG. 10). The treatment time duration (500, 600, 700, 1000) is configured to span a part of (or identified in) the electrocardiogram tracing 300 that was generated. The tissue layer (such as, the pericardium layer) is treatable (puncturable) during, at least in part, the treatment time duration (500, 600, 700, 1000). This is done in such a way that inadvertent damage to the tissue (which is not to be treated or negatively impacted) located adjacent to the tissue layer (the pericardium layer) is reduced (preferably avoided) while the tissue layer (the pericardium layer) is treated during the treatment time duration (500, 600, 700, 1000). More preferably, the computer system 200 is also configured to identify (compute, calculate) the treatment time duration (500, 600, 700, 1000) configured to span a part of (or identified in) the electrocardiogram tracing 300 that was generated. The tissue layer (the pericardium layer) is treatable during, at least in part, the treatment time duration (500, 600, 700, 1000). This is done in such a way that, during, at least in part, the treatment time duration (500, 600, 700, 1000), the blood pressure within the heart urges the tissue layer (pericardium layer) to impart a relatively lower amount of tissue force toward the treatment device while: (A) the treatment device is positioned proximate to the tissue layer (the pericardium layer), and (B) the treatment device is activated (used) to treat the tissue layer (pericardium layer). The computer system 200 is also configured to provide (write, output, transmit) the treatment time duration (500, 600, 700, 1000) that was identified (computed).

Referring to the embodiment as depicted in FIG. 1, there is provided an apparatus for use with an electrocardiogram signal configured to indicate (provide) a cardiac cycle of the heart, of a patient, having the pericardium layer, of the heart, that is puncturable by a puncture device 102. The apparatus includes a computer system 200 configured to receive (read, input) the electrocardiogram signal, from an electrocardiographic sensor. The electrocardiogram signal is configured to indicate (provide) the cardiac cycle of the heart having the pericardium layer to be punctured by the puncture device 102. The computer system 200 is also configured to generate (compute, calculate) an electrocardiogram tracing 300 based on the electrocardiogram signal that was received. The computer system 200 is also configured to identify (compute, calculate) a treatment time duration (500, 600, 700, 1000) (as depicted in FIG. 5, FIG. 6, FIG. 7 or FIG. 10). The treatment time duration (500, 600, 700, 1000) is configured to span a part of (or identified in) the electrocardiogram tracing 300 that was generated. The pericardium layer is puncturable during, at least in part, the treatment time duration (500, 600, 700, 1000) in such a way that, during, at least in part, the treatment time duration (500, 600, 700, 1000), the blood pressure within the heart urges the pericardium layer to impart a relatively lower amount of tissue force toward the puncture device 102 while (A) the puncture device 102 is positioned proximate to the pericardium layer, and (B) the puncture device 102 is activated to puncture the pericardium layer. Advantageously, inadvertent damage to the tissue located adjacent to the pericardium layer is reduced (preferably avoided) while the pericardium layer is punctured during the treatment time duration (500, 600, 700, 1000). The computer system 200 is also configured to provide (write, output, transmit) the treatment time duration (500, 600, 700, 1000) that was identified (computed).

Referring to the embodiment as depicted in FIG. 1, the apparatus is adapted such that the computer system 200 is also configured to provide user-feedback configured to indicate (provide) a start time and a stop time of the treatment time duration (500, 600, 700, 1000) (as depicted in FIG. 5, FIG. 6, FIG. 7 or FIG. 10). Puncturing of the pericardium layer (by the puncture device 102) may start after the beginning of the treatment time duration (500, 600, 700, 1000). Puncturing of the pericardium layer (by the puncture device 102) may stop (end) before the ending of the treatment time duration (500, 600, 700, 1000).

Referring to the embodiment as depicted in FIG. 1, the apparatus is adapted such that the puncture device 102 includes an energy-emitting puncture device 103 (such as, a radio-frequency energy-emitting device, etc., and any equivalent thereof). The computer system 200 and the energy-emitting puncture device 103 are configured to be in signal communication with each other. The computer system 200 is also configured to transmit the treatment time duration (500, 600, 700, 1000), as depicted in FIG. 5, FIG. 6, FIG. 7 or FIG. 10, to the energy-emitting puncture device 103. Advantageously, usage of the computer system 200 may result in a safer (lower) amount of application force to be imparted to the tissue from the energy-emitting puncture device 103 while energy is selectively emitted to the tissue. The physician may be more confident that an optimal contact force is achieved by applying (emitting) energy during a specific time interval.

Referring to the embodiment as depicted in FIG. 1, the apparatus is adapted such that the energy-emitting puncture device 103 is configured to puncture the pericardium layer by selectively emitting energy, to the pericardium layer, during, at least in part, the treatment time duration (500, 600, 700, 1000), as depicted in FIG. 5, FIG. 6, FIG. 7 or FIG. 10. The energy-emitting puncture device 103 is configured to stop the emission of energy, to the pericardium layer, before the end of the treatment time duration (500, 600, 700, 1000).

Referring to the embodiment as depicted in FIG. 1, the apparatus is adapted such that the computer system 200 is also configured to transmit an energy-activation signal to the energy-emitting puncture device 103, in which the energy-activation signal is configured to activate the emission of energy from the energy-emitting puncture device 103 so that the energy-emitting puncture device 103, in use, is urged to selectively emit energy during, at least in part, the treatment time duration (500, 600, 700, 1000) (as depicted in FIG. 5, FIG. 6, FIG. 7 or FIG. 10).

Referring to the embodiment as depicted in FIG. 1, in accordance with an embodiment, the apparatus may be adapted such that the energy-emitting puncture device 103 (or the puncture device 102) is configured to be in signal communication with, either directly or indirectly, the computer system 200. In accordance with another embodiment, the apparatus may be adapted such that the energy-emitting puncture device 103 (or the puncture device 102) is configured to be in signal communication with, either directly or indirectly, the computer system 200, and the energy-emitting puncture device 103 (or the puncture device 102) is configured to receive the electrocardiogram signal (from the heart of the patient). In accordance with yet another embodiment, the apparatus may be adapted such that the energy generator 118 (which is configured to be in signal communication with, either directly or indirectly, the puncture device 102 or the energy-emitting puncture device 103) includes the computer system 200. In accordance with yet another embodiment, the apparatus may be adapted such that the pulse generator 116 (which is configured to be in signal communication with, either directly or indirectly, the puncture device 102 or the energy-emitting puncture device 103) includes the computer system 200.

Referring to the embodiment as depicted in FIG. 1, the puncture device 102 may also be configured to be used as a guidewire (if desired). The guidewire is a device used to enter tight spaces, obstructed valves or channels, within the body, or to assist in inserting, positioning, and moving a catheter. The puncture device 102 may include an elongated shaft 104 having a proximal end 106 and a distal end 108. An energy-emitting element 110 (also called an electrode) is positioned (mounted) at the distal end 108. The energy-emitting element 110 is configured to selectively emit energy (such as, radio-frequency energy). In accordance with an embodiment, the energy-emitting element 110 (or the puncture device 102) is configured to receive the electrocardiogram signal (from the heart of the patient).

Referring to the embodiment as depicted in FIG. 2, the elongated shaft 104 may include a wire 112 and a layer of electrical insulation 114 positioned on (covering) the wire 112. The energy-emitting element 110 is, preferably, in the form of an electrically exposed end of the wire 112. The energy-emitting element 110 is configured to (A) deliver (emit) a stimulus signal to the tissue, and (B) deliver (emit) energy (radio-frequency energy) of sufficient strength or intensity to puncture the tissue (as will be described below). The elongated shaft 104 is, preferably, resiliently flexible. The elongated shaft 104 is biased towards a generally straight configuration. The elongated shaft 104 may also be curved or bent with the application of force. When force is removed from the elongated shaft 104, the elongated shaft 104 is configured to move back towards a straight configuration. For alternative embodiments, the elongated shaft 104 may be relatively stiff (that is, the elongated shaft 104 may be of a similar stiffness to that of a medical needle, etc.).

Referring to the embodiment as depicted in FIG. 1, the system 100 further includes a pulse generator 116. The system 100 further includes an energy generator 118 (such as, a radio-frequency generator). The energy-emitting element 110 is electrically connected to the pulse generator 116 and the energy generator 118 via a wire 112 (as depicted in FIG. 2). The pulse generator 116 is configured to generate a stimulus signal. The energy-emitting element 110 is configured to receive the stimulus signal and deliver the stimulus signal to the tissue with which the energy-emitting element 110 is in contact therewith (such as, the pericardium of the heart, etc.). When delivered to the heart, the stimulus signal may force contraction and/or transient standstill (relaxation) of the heart (such as, when or while the heart is in a contracted state. The stimulus signal may be a rapid-pacing signal, etc., and any equivalent thereof. In accordance with a preferred embodiment, the pulse generator 116 includes the MICROPACE (TRADEMARK) system manufactured or sold by GE HEALTHCARE COMPANY (based in the United States). The energy generator 118 is configured to generate energy (such as, radio-frequency energy, etc., and any equivalent thereof). The energy-emitting element 110 is configured to receive the energy from the energy generator 118 and deliver the energy to the tissue with which the energy-emitting element 110 is in contact therewith (that is, in contact with the pericardium of the heart). When delivered to the tissue, the energy may cause (form) a puncture extending (at least in part) through the tissue. In accordance with a preferred embodiment, the energy generator 118 includes the Model RFP-100A RF puncture generator manufactured by the BAYLIS MEDICAL COMPANY Inc. (based in Montreal, Canada). The energy generator 118 may be connected to one or more grounding pads (not shown and known to persons skilled in the art), etc.

Referring to the embodiment as depicted in FIG. 1, the puncture device 102 is electrically connected (preferably, directly electrically connected) to the energy generator 118 at the proximal end 106 of the elongated shaft 104. The energy generator 118 is configured to be electrically connected to the pulse generator 116 by a cable 120. This is done in such a way that the puncture device 102 is indirectly electrically connected to the pulse generator 116 via the energy generator 118. Electrically connecting the energy generator 118 and the pulse generator 116 is configured to facilitate signal communication between the energy generator 118 and the pulse generator 116. The is done in such a way that (A) reception of the electrocardiogram signal (from the heart of the patient), and (B) the delivery (emission, transmission) of energy (to the tissue) may be coordinated at the correct or desired time duration (so that the puncture may be formed, at least in part, through the pericardium of the heart without causing inadvertent damage to tissue that is adjacently located to the pericardium of the heart).

Referring to the embodiment as depicted in FIG. 1, for alternative embodiments, the puncture device 102 may be (A) directly electrically connected to both the energy generator 118 and the pulse generator 116, or (B) indirectly electrically connected to both the energy generator 118 and the pulse generator 116 (e.g. via an accessory device), or (C) directly electrically connected to the pulse generator 116 and indirectly electrically connected to the energy generator 118 via the pulse generator 116, etc., and any equivalent thereof.

Referring to the embodiment as depicted in FIG. 1, the electrocardiogram monitoring (ECG monitoring or EKG monitoring) may be done (performed or completed) via the puncture device 102 (that is, via the energy-emitting element 110), and any equivalent thereof. For instance, an equivalent may include utilizing another known device positioned proximate to the heart, and also configured to receive the electrocardiogram signal from the heart. The other known device is spaced apart from the puncture device 102 (or the energy-emitting element 110).

Referring to the embodiment as depicted in FIG. 1, the energy-emitting element 110 is (preferably) further configured to serve (act) as an electrocardiogram electrode configured to receive an electrocardiogram signal from the heart (after the energy-emitting element 110 is positioned proximate to the heart). The energy-emitting element 110 is further configured to (A) detect (receive) an electrocardiogram signal from the heart (of the patient, not depicted), and (B) selectively deliver (transmit) the electrocardiogram signal to an electrocardiogram-monitoring system (not shown and known to persons of skill in the art), in which the electrocardiogram-monitoring system is configured to cooperate with the puncture device 102.

Referring to the embodiment as depicted in FIG. 1, the puncture device 102 may include any type of tip configuration, such as a straight tip, etc. The puncture device 102 may include a medical needle (also called a catheter device) configured to follow a guidewire (such as, after the puncture is formed). The puncture device 102 is configured to acquire an electrocardiogram signal. The puncture device 102 may be bipolar with various electrode configurations (such as, one electrode at the tip of the puncture device and another on the introducer, or two electrodes on the puncture device, etc.).

Referring to the embodiment as depicted in FIG. 1, the puncture device 102 may cooperate with an introducer device (known and not depicted). The introducer may be made of a variety of materials such as a combination of high-density polyethylene (HDPE), low-density polyethylene (LDPE), a combination of the PEBAX (TRADEMARK) elastomer (manufactured by the ARKEMA Company), nylon, nylon 12 (which is made from o-aminolauric acid or laurolactam monomers that each have 12 carbons), preferably with braiding, etc. The introducer may be steerable, in which case a pull ring with pull wires may be included in the shaft, and a control mechanism may be included in the handle, etc. The introducer may have a luer cap to connect to the introducer luer. The introducer may include a stylet configured to be advanced along the introducer to the heart (once contact with the heart is made, the stylet is exchanged for a radio-frequency energy device, etc.). The introducer may be configured to have echogenicity. The introducer may include a coil to improve echogenicity. Echogenicity or echogeneity is the ability to bounce an echo, e.g. return the signal in ultrasound examinations. In other words, echogenicity is higher when the surface bouncing the sound echo reflects increased sound waves. The introducer may include a shaft that may have a lubricious coating to increase tactile feedback. The introducer may include a hemostasis valve and/or a three-way stopcock. The introducer assembly may be configured to have radiopacity. The introducer assembly may include a radiation band (such as, a platinum band, an iridium band) to improve radiopacity. Radiodensity (or radiopacity) is opacity to the radio wave and X-ray portion of the electromagnetic spectrum: that is, the relative inability of those kinds of electromagnetic radiation to pass through a particular material.

Referring to the embodiment as depicted in FIG. 1, an equivalent to the radio-frequency puncture generator is an electrosurgical generator. The physician may control the amount and time of energy delivery manually, but manual arrangement is not recommended as reduced fidelity in timing may increase risk to adverse events.

Figure 3:
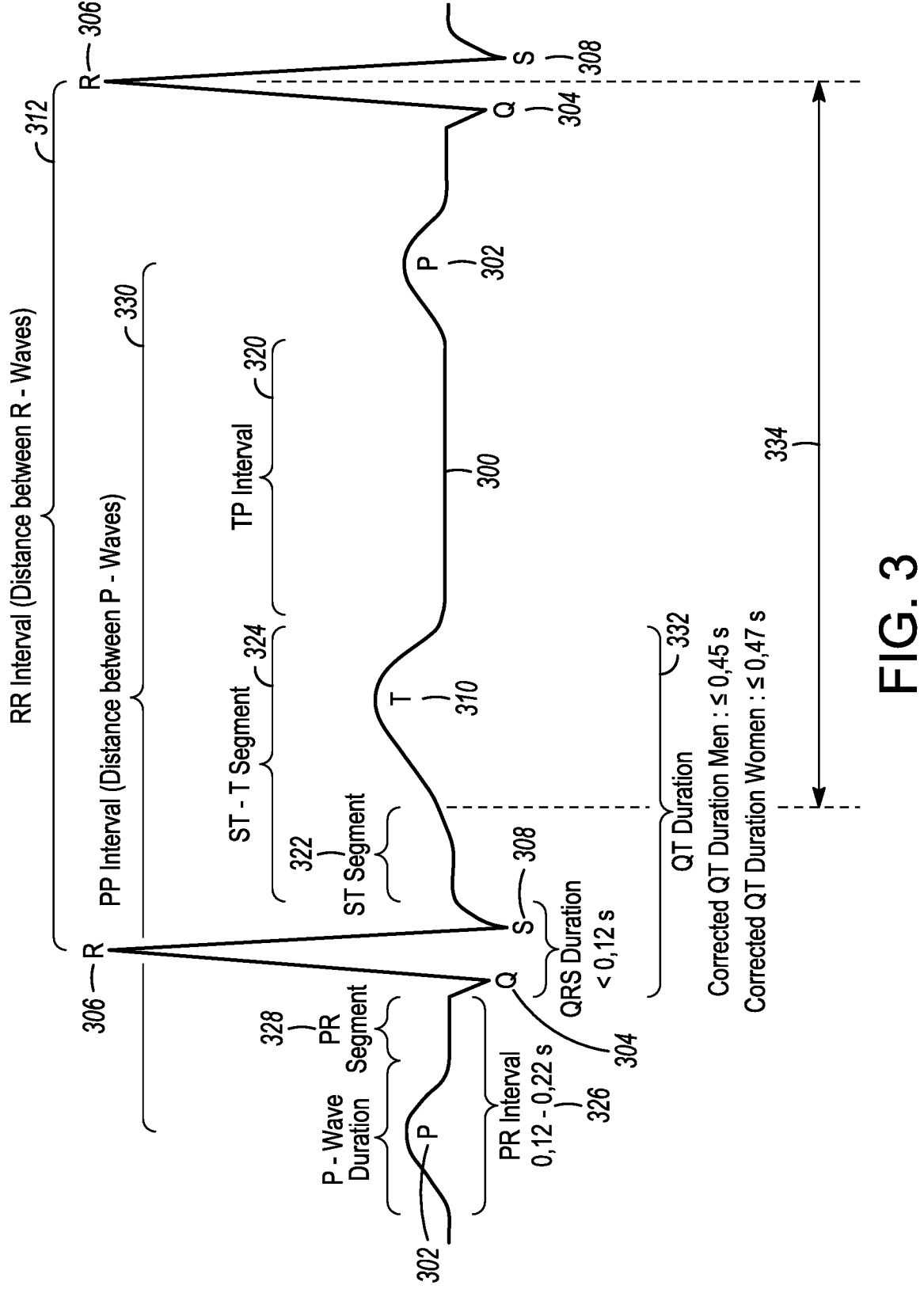
FIG. 3 depicts a schematic view of an embodiment of an electrocardiogram tracing, which may be used by the puncture device of FIG. 1.

Referring to the embodiment as depicted in FIG. 1, there is provided a method for forming a pericardial puncture. The method includes a step (a): contacting the pericardium of the heart of the patient with the energy-emitting element 110 of the puncture device 102. The method also includes a step (b): delivering (emitting), while the heart is in a contracted state, energy (such as radio-frequency energy) from the energy-emitting element 110 to the tissue for the purpose of forming a puncture through the pericardium of the heart. In accordance with an option, prior to step (b), the method may further include delivering a stimulus signal to the heart to force contraction (of the heart) and/or transient standstill (relaxation) of the heart (preferably when the heart is in the contracted state). In accordance with a further option, prior to step (b), the method may further include monitoring of a signal (such as, an electrocardiogram tracing 300 of a cardiac cycle of the heart, as depicted in FIG. 3) to be provided (generated) by the electrocardiogram system (also called an electrocardiography system). The electrocardiogram system is configured to be connected to measure or receive the signal from the heart. The signal may be used to determine when the heart is in the contracted state. Then energy is applied to the tissue accordingly (apply energy to the pericardium layer) in a relatively safer manner, thereby avoiding inadvertent or unwanted application of energy that might damage the tissue located proximate to the tissue receiving the treatment (such as the pericardium layer, etc.).

Referring to the embodiment as depicted in FIG. 1, an arrangement may be made for electrocardiogram recording pass-through. The physician may connect the energy-emitting device to a radio-frequency puncture generator pass-through port or to a duo-mode box. It is possible to connect the energy-emitting device directly to the electrocardiogram system, but may need to be disconnected before the application (emission) of energy, thereby potentially removing the benefit of timing for the application of energy to tissue.

Referring to the embodiment as depicted in FIG. 1, an arrangement may be made for electrocardiogram filtering and signal enhancement of the electrocardiogram signal. An increase in fidelity in timing may be done through signal processing (enhancement) to better delineate the beginning of the RR-interval 312 (as depicted in FIG. 3). It may be possible to use a raw signal from the distal tip of the puncture device 102.

Referring to the embodiment as depicted in FIG. 1, an equivalent of the puncture device 102 may include an electrosurgical unit (ESU) that includes a generator and a hand piece with one or more electrodes. A switch is configured to control the electrosurgical unit, and the switch may be positioned on a hand piece, a foot switch, etc. The electrosurgical generator may produce a variety of electrical waveforms. As these waveforms change, so do the corresponding tissue effects.

FIG. 3 depicts a schematic view of an embodiment of an electrocardiogram tracing 300, which may be used by the puncture device 102 of FIG. 1 (for the timing of when a puncture may be formed or when a treatment may be applied by a treatment device, etc.).

Referring to the embodiment as depicted in FIG. 3, the electrocardiogram tracing 300 (also called an electrocardiogram tracing 300, etc.) may be generated by an electrocardiogram system (also called an ECG system, an EKG system, etc.) configured to be operatively connected (via leads and a sensor assembly) to the heart of a patient, etc. The electrocardiogram system is known to persons of skill in the art and, is therefore, not depicted and not described with specific details.

Referring to the embodiment as depicted in FIG. 3, the electrocardiogram tracing 300 (also called the ECG signal pattern or a waveform) may be used for any one of the following durations: (a) distinguishing between the systole phase and the diastole phase, (b) identifying isovolumetric contraction, (c) identifying ejection, (d) identifying isovolumetric relaxation, (e) identifying rapid inflow, (f) identifying diastasis, and (g) identifying atrial systole. The diastole phase and the systole phase are two phases of the cardiac cycle of the heart. The diastole phase and the systole phase occur as the heart beats, and pumps blood through blood vessels that carry blood to the body of the patient. The systole phase occurs when the heart contracts to pump blood out. The diastole phase occurs when the heart relaxes after contraction. During the systole phase, the heart enters isovolumetric contraction in which the heart pumps out, on average, 60 percent of its blood volume resulting in a displacement of heart tissue within the pericardial sack.

Referring to the embodiment as depicted in FIG. 3, the electrocardiogram system (ECG system or EKG system) is configured to detect electrical signals (electrocardiogram signals) of the heart. The electrocardiogram system (known and not depicted) is also configured to produce (generate) signal information (regarding a cardiac cycle), such as the electrocardiogram tracing 300 (also called an electrocardiogram waveform, an ECG waveform, an EKG waveform, etc.). The electrocardiogram tracing 300 is configured to depict (provide) a graphical representation (signal amplitude versus time along the horizontal axis) of the electrical signals (electrocardiogram signals) of the heart beating over a time duration. The electrocardiogram tracing 300 is a tracing configured to represent the electrical activity that takes place within the heart of the patient. For each heartbeat, an electrical signal (electrical impulse) travels through the heart of the patient. Under normal circumstances, the electrical impulse may travel from the sinoatrial node, spread across the atrium of the heart, to the atrioventricular node and through the ventricular septum of the heart. The electrical impulse causes the four chambers of the heart to alternatively contract and relax in a coordinated (cooperative) fashion. Studying the electrical impulses (outlined in the electrocardiogram tracing 300) allows for an understanding of how the heart is functioning (and this may help the physician to make a diagnosis of potential negative health issues, if any). There are phases of the cardiac cycle which represent a single heartbeat. Each heartbeat may include the P-wave 302, the QRS-complex (304, 306, 308) and the T-wave 310. The QRS-complex (304, 306, 308) includes a combination of three (distinct) graphical deflections or waves, such as the Q-wave 304, the R-wave 306 and the S-wave 308. The Q-wave 304 represents septal depolarization of the heart. The R-wave 306 represents ventricular depolarization. The S-wave 308 represents depolarization of the Purkinje fibres. The QRS-complex (304, 306, 308) is (usually) the central and most visually obvious part of the electrocardiogram tracing 300. The QRS-complex (304, 306, 308) is the main spike seen on the electrocardiogram tracing 300. The QRS-complex (304, 306, 308) corresponds to the depolarization of the right and left ventricles of the heart and the contraction of the large ventricular muscles of the heart. In adults, the QRS-complex (304, 306, 308) may last about 80 ms (milliseconds) to about 100 ms. The Q-wave 304, the R-wave 306 and the S-wave 308 occur in rapid succession, do not all appear in all leads, and reflect a single event and, thus, are usually considered together. The QRS-complex (304, 306, 308) represents the electrical impulse signal as the electrical impulse spreads through the ventricles (of the heart). The QRS-complex represents ventricular depolarization. As with the P-wave 302, the QRS-complex (304, 306, 308) starts just before ventricular contraction. However, not every QRS-complex (304, 306, 308) may contain the Q-wave 304, the R-wave 306 and the S-wave 308. A QRS detector (known and not depicted) may be utilized to detect QRS signals of the heart. The Q-wave 304, the R-wave 306 and the S-wave 308 of the QRS-complex (304, 306, 308) occur in rapid succession. As with the P-wave 302, the QRS-complex (304, 306, 308) starts just before ventricular contraction. Ventricular activation and depolarization is represented by the QRS-complex (304, 306, 308), whereas ventricular repolarization (VR) is expressed as the interval between the beginning of the QRS-complex (304, 306, 308) to the end of the T-wave 310 (the QT-duration 332, which may be referred to as the QT-interval). The convention is that the Q-wave 304 is always negative and that the R-wave 306 is the first positive wave of the complex. For the case where the QRS-complex (304, 306, 308) only includes an upward (positive) deflection, then it is the R-wave 306. The S-wave 308 is the first negative deflection after the R-wave 306. In neuroscience, repolarization refers to the change in membrane potential that returns it to a more negative value just after the depolarization phase of an action potential which has changed the membrane potential to a more positive value. Depolarization is the action potential in a neuron, in which the cell's internal charge becomes less negative (more positive), and repolarization is where the internal charge returns to a more negative value (less positive).

Referring to the embodiment as depicted in FIG. 3, the P-wave 302 represents the depolarization (atrial depolarization) of the left atrium and the right atrium (the atria of the heart), and also corresponds to atrial contraction. The atria may contract very soon after the P-wave 302 begins. Because the P-wave 302 is so small, atrial repolarization is usually not visible on the electrocardiogram tracing 300 (ECG measurement, trace, waveform). In most cases, the P-wave 302 may be smooth and rounded. When the valves (of the heart) between the atria and the ventricles open, about 70 percent of the blood in the atria falls through with the aid of gravity, but mainly due to suction caused by the ventricles as they expand. Atrial contraction is required only for the final about 30 percent (of a heartbeat), and, therefore, a relatively small muscle mass is required (for contraction), and a relatively small amount of voltage is needed to contract the atria of the heart.

Referring to the embodiment as depicted in FIG. 3, the Q-wave 304 is a small negative wave immediately before the QRS-complex (304, 306, 308). While the electrical stimulus passes through the His bundle (also called the bundle of His), and before it separates down the two bundle branches, it starts to depolarise the septum from left to right. The bundle of His is a collection of heart muscle cells specialized for electrical-signal conduction that travels in the opposite direction to the main conduction (right to left) so the Q-wave 304 points in the opposite direction to the QRS-complex (304, 306, 308).

Referring to the embodiment as depicted in FIG. 3, the R-wave 306 represents the electrical stimulus as it passes through the main portion of the ventricular walls (of the heart). The walls of the ventricles are relatively thicker due to the amount of work they have to do and, consequently, more voltage is required. This is why the R-wave 306 is by far the biggest wave generated during normal conduction. There are many ways to determine a patient's heart rate when using the electrocardiogram tracing 300 (ECG waveform). One way is called the sequence method. To use the sequence method, the technician finds the R-wave 306 that lines up with one of the darker vertical lines plotted (depicted) on the electrocardiogram tracing 300 (such as, the ECG paper printout, etc.). For instance, if the next instance of the R-wave 306 appears on the next dark vertical line, this appearance may correspond to a heart rate of about 300 beats per minute (bpm). The dark vertical lines may correspond to 300 bpm, 150 bpm, 100 bpm, 75 bpm, 60 bpm and 50 bpm, etc. For example, if there are three large boxes between two instances of the R-wave 306, the patient's heart rate is 100 bpm (beats per minute). There are more accurate ways to determine heart rate from the electrocardiogram tracing 300, but in life-saving scenarios, this method provides a quick estimate.

Referring to the embodiment as depicted in FIG. 3, the S-wave 308 is a small negative wave following the R-wave 306. The S-wave 308 represents depolarization in the Purkinje fibres (of the heart). The S-wave 308 travels in the opposite direction to the R-wave 306 because the Purkinje fibres spread throughout the ventricles from top to bottom and then back up through the walls of the ventricles.

Referring to the embodiment as depicted in FIG. 3, the T-wave 310 follows the QRS-complex (304, 306, 308). The T-wave 310 indicates ventricular repolarization. Both ventricles repolarise before the cycle repeats itself and therefore the T-wave 310 is visible. Unlike the P-wave 302, a normal instance of the T-wave 310 is slightly asymmetric. The peak of the T-wave 310 is a little closer to its end than to its beginning. The T-wave 310 may normally follow the same direction as the QRS-complex (304, 306, 308) that preceded it (positive or negative, up or down). When the T-wave 310 occurs in the opposite direction of the QRS-complex (304, 306, 308), the T-wave 310 may indicate cardiac pathology.

Referring to the embodiment as depicted in FIG. 3, the ST-segment 322 is a period (of time) located between the end of the QRS-complex (304, 306, 308) and the beginning of the T-wave 310. The ST-segment 322 represents the beginning of ventricular repolarization where there is no electrical conduction, or may be located between the end of the S-wave 308 (also called the J-point) and the beginning of the T-wave 310). The ST-segment 322 is a (substantially) flat isoelectric section of the electrocardiogram tracing 300. The ST-segment 322 is a key indicator for either one of (or both) myocardial ischemia and/or myocardial necrosis (in which case, the ST-segment 322 either shifts upwardly or downwardly, etc.). The ST-segment 322 represents the interval between ventricular depolarization and repolarization. Myocardial ischemia occurs when blood flow to the heart muscle (myocardium) is obstructed by a partial or complete blockage of a coronary artery by a buildup of plaque material (atherosclerosis). Myocardial necrosis refers to the cell death of cardiomyocytes and is defined by an elevation of cardiac troponin values.

Referring to the embodiment as depicted in FIG. 3, the J-point (also called a junction) is the point where the QRS-complex (304, 306, 308) and the ST-segment 322 meet. The J-point is the start of the ST-segment 322. The J-point may be used to diagnose an elevation of the ST-segment 322 (due to myocardial infarction). When the J-point is elevated at least by a predetermined distance (such as, about two millimetres above the baseline), it is indicative of an STEMI (ST-segment elevation myocardial infarction). The ST-segment elevation myocardial infarction is a serious form of heart attack in which a coronary artery is completely blocked and a large part of the heart muscle is unable to receive blood. Elevation of the ST-segment 322 (ST-segment elevation) refers to a pattern that may show up on the electrocardiogram tracing 300.

Referring to the embodiment as depicted in FIG. 3, for the case where a relatively small wave occurs between the T-wave 310 and the P-wave 302, the small wave may be the U-wave (not depicted and known). The biological basis for a U-wave is unknown. In some cases, the U-wave may follow the T-wave 310. It is possible to see another wave after the PQRST complex (that is, the combination of the P-wave 302, the Q-wave 304, the R-wave 306, the S-wave 308 and the T-wave 310). The U-wave is not very common and may, therefore, be easy to overlook. For a normal heartbeat, the T-wave 310 represents repolarization of the ventricles, specifically the repolarization of the atrioventricular node (AV node) and the bundle branches of the heart. The U-wave occurs when the electrocardiogram system (not depicted but known) picks up (receives) a signal associated with the repolarization of the Purkinje fibres of the heart. The U-wave may occur, for instance, as a result of electrolyte imbalances (imbalances in potassium levels).

Referring to the embodiment as depicted in FIG. 3, the cardiac cycle includes an isovolumetric ventricular contraction phase, a rapid ejection phase, a reduced ejection phase, an isovolumetric relaxation phase, a ventricular filling phase and an atrial contraction phase.

Referring to the embodiment as depicted in FIG. 3, the isovolumetric ventricular contraction phase marks the beginning of the systole phase, and starts with the appearance of the QRS-complex on the electrocardiogram tracing 300, and the closure of the atrioventricular valves. Systole (systole phase) is a period of contraction of the ventricles of the heart that occurs between the first and second heart sounds of the cardiac cycle (the sequence of events in a single heart beat). Systole causes the ejection of blood into the aorta and pulmonary trunk. With all valves of the heart closed, the ventricle generates positive pressure without any change in its volume (isovolumetric) to overcome the opening resistance of the semilunar valves. The systole phase usually lasts for about six percent of the cardiac cycle.

Referring to the embodiment as depicted in FIG. 3, for the rapid ejection phase, as the semilunar valves open, there is a rapid ejection of blood due to increased ventricular contractility. The arterial pressure increases until reaching a maximum. The rapid ejection phase usually lasts for about 13 percent of the cardiac cycle.

Referring to the embodiment as depicted in FIG. 3, the reduced ejection phase marks the beginning of ventricular repolarization as depicted by the onset of the T-wave 310 on the electrocardiogram tracing 300. Repolarization leads to a rapid decline in ventricular pressures and hence the reduced rate of ejection (of blood). However, some forward flow of blood continues secondarily to the remnant kinetic energy from the previous phase. The reduced ejection phase usually lasts for about 15 percent of the cardiac cycle.

Referring to the embodiment as depicted in FIG. 3, for the isovolumetric relaxation phase, when the ventricular pressures drop below the diastolic aortic pressure and the pulmonary pressure, the aortic and pulmonary valves close producing the second heart sound. This marks the beginning of diastole. The ventricles generate negative pressure without changing their volume (isovolumetric) so that the ventricular pressure becomes lower than the atrial pressure. The isovolumetric relaxation phase usually lasts for about eight percent of the cardiac cycle.

Referring to the embodiment as depicted in FIG. 3, for the ventricular filling phase, as the atrioventricular valves open, ventricular filling starts. The initial rapid filling is mainly augmented by ventricular suction which results from ventricular untwisting and the return of each ventricular muscle fiber to its slack length. The ventricular pressure gradually increases until it equals the atrial pressure and the atrioventricular valves close. The ventricular filling phase usually lasts for about 44 percent of the cardiac cycle.

Referring to the embodiment as depicted in FIG. 3, for the atrial contraction phase, near the end of ventricular diastole, the atrial contraction contributes about 10 percent of the ventricular filling volume. This is represented by the P-wave 302 located on the following cardiac cycle or heartbeat (indicated in the electrocardiogram tracing 300). The atrial contraction phase lasts for about 14 percent of the cardiac cycle.

Figure 4A:
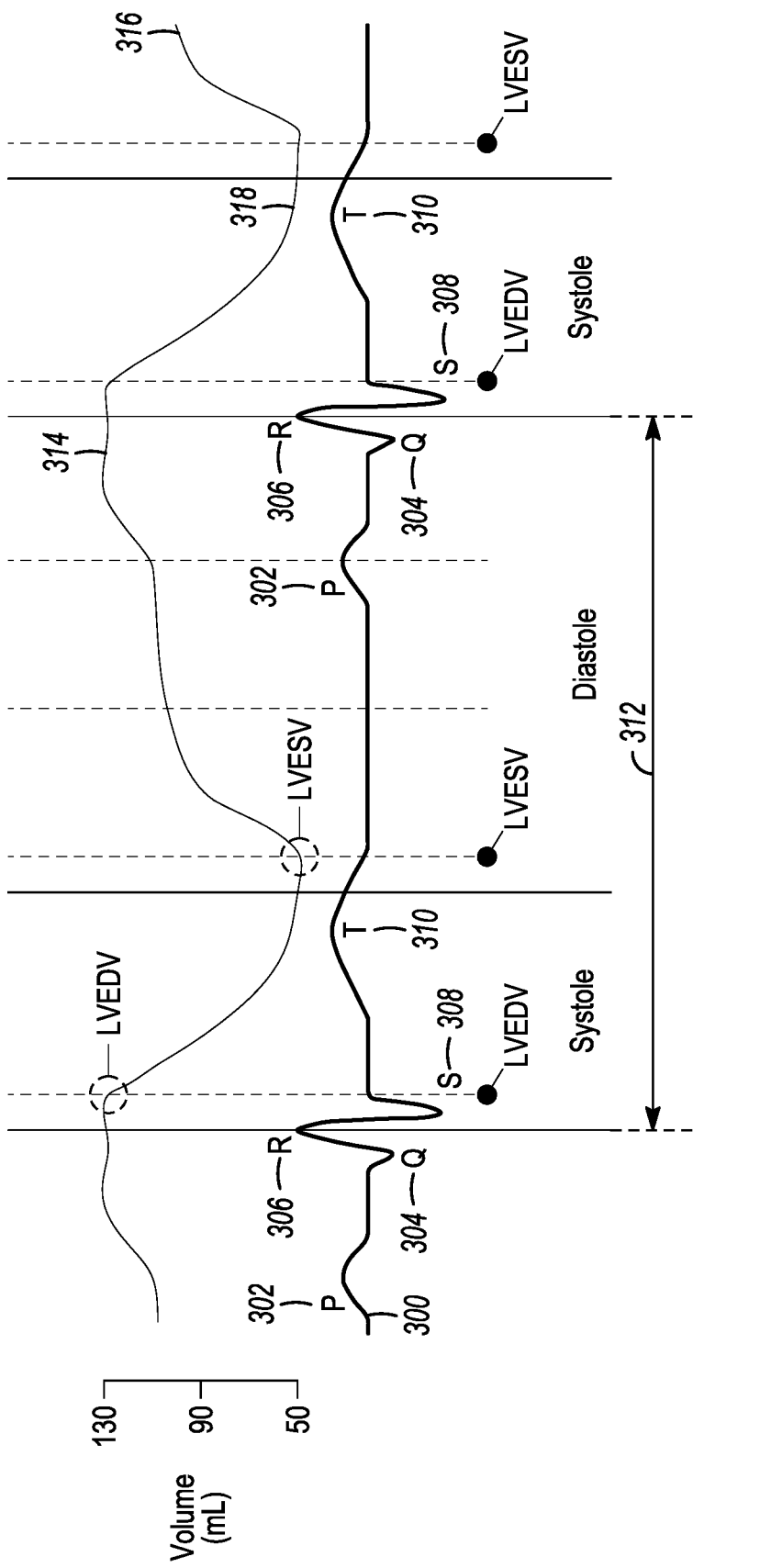
FIG. 4A and FIG. 4B depict a schematic view of an embodiment of an electrocardiogram tracing of a cardiac cycle of the heart of the patient (as depicted in FIG. 4A), and tenting of the ventricle (of the heart) during systole (in FIG. 4B)

Referring to the embodiment as depicted in FIG. 3 and FIG. 4A, there is depicted an embodiment of the electrocardiogram tracing 300. The electrocardiogram tracing 300 includes (a delineation of) the RR-interval 312 (as depicted in FIG. 3). The RR-interval 312 is the time between heartbeats. The RR-interval 312 may be used to calculate heart rate. The normal range for the RR-interval 312 is from about 0.6 seconds to about 1.0 second, with a corresponding heart rate from about 60 to about 100 beats per minute. The beginning of the RR-interval 312 may be marked by the left ventricular end-diastolic volume (also called, the peak blood volume 314, as depicted in FIG. 4A), which then declines over about 0.4 seconds to the minimum blood volume (the left ventricular end systolic volume). The end systolic volume (ESV) is the volume of blood in the ventricle at the end of contraction (or the systole phase), and the beginning of filling (or diastole). The end systolic volume is the lowest volume of blood in the ventricle at any point in the cardiac cycle. The main factors that affect the end systolic volume are afterload and the contractility of the heart. The RR-interval 312 is the time elapsed between two successive (adjacent) instances of the R-waves 306 formed on (part of) the electrocardiogram tracing 300 (which was generated by the electrocardiogram system), and its reciprocal, the heart rate (HR). The RR-interval 312 is a function of intrinsic properties of the sinus node (of the heart) as well as autonomic influences (involuntary influences relating to the autonomic nervous system). The sinus node is an area of specialized cells in the upper right chamber of the heart. The sinus node controls the rhythmic contractions (the heartbeat) of the heart. Under normal conditions, the sinus node creates a steady pace of electrical impulses. The beginning of the RR-interval 312 is marked by the crest of the R-wave 306 (also called the R-wave crest). The crest of the R-wave 306 corresponds to the peak blood volume 314 (as depicted in FIG. 4A) and a period (phase) of isovolumetric contraction (IC). The peak blood volume 314 is shown in the ventricular volume line 316 (as depicted in FIG. 4A). The peak blood volume 314 then declines over approximately 0.4 seconds to the minimum blood volume 318 (as depicted in FIG. 4A) and a period of isovolumetric relaxation (IR).

Referring to the embodiment as depicted in FIG. 3 and FIG. 4A, there is depicted the TP-interval 320. During the TP-interval 320 (also called the TP segment), the ventricles begin to re-fill to the peak blood volume 314 (as depicted in FIG. 4A) again before reaching a period (phase) of isovolumetric contraction (IC). The TP-interval 320 is the portion of the electrocardiogram tracing 300 from the end of the T-wave 310 to the beginning of the P-wave 302. The TP-interval 320 should always be at baseline and is used as a reference to determine whether the ST-segment 322 is elevated or depressed, as there are no specific disease conditions that elevate or depress the TP-interval 320.

Referring to the embodiment as depicted in FIG. 3, the PR-interval 326 is the time from the onset of the P-wave 302 to the start of the QRS-complex (304, 306, 308). The PR-interval 326 reflects electrical conduction through the atrioventricular node (AV).

Referring to the embodiment as depicted in FIG. 3, the PR-segment 328 is the flat, usually isoelectric segment, between the end of the P-wave 302 and the start of the QRS-complex (304, 306, 308).

Referring to the embodiment as depicted in FIG. 3, the PP-interval 330 (also called the P-P interval) is the time between successive instances or adjacent occurrences (instances) of the P-wave 302.

Referring to the embodiment as depicted in FIG. 3, the QT-duration 332 (also called the QT-interval) is a measurement made on (derived from) the electrocardiogram tracing 300. The QT-duration 332 may be used to assess some of the electrical properties of the heart. The QT-duration 332 is calculated (measured) as the time from the start of the Q-wave 304 to the end of the T-wave 310. The QT-duration 332 approximates to the time taken from when the cardiac ventricles start to contract to when they finish relaxing.

Figure 4B:
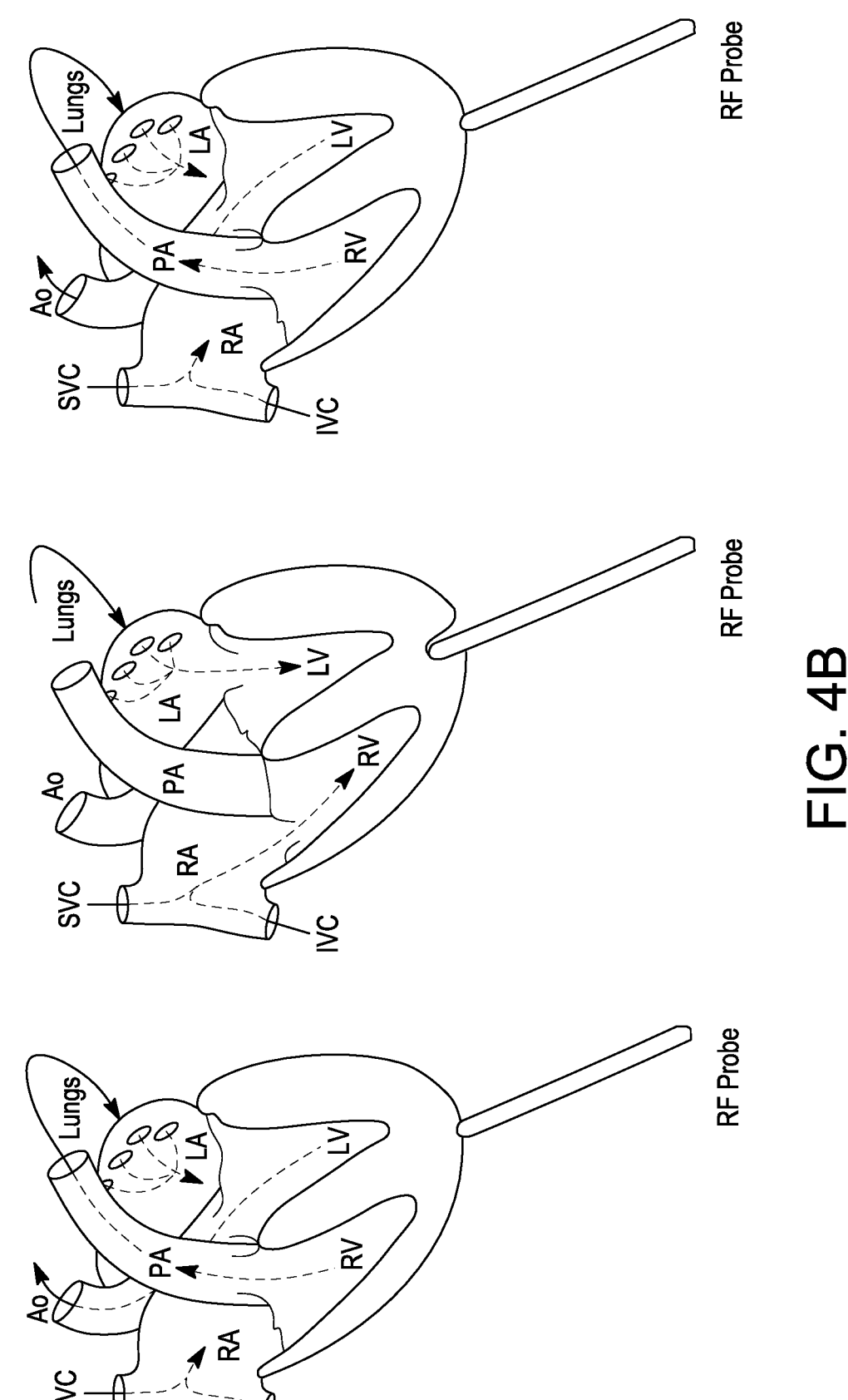

FIG. 4A and FIG. 4B depict a schematic view of an embodiment of an electrocardiogram tracing 300 of a cardiac cycle of the heart of the patient (as depicted in FIG. 4A), and tenting of the ventricle (of the heart) during systole (in FIG. 4B).

Referring to the embodiment as depicted in FIG. 4A, the end-diastolic volume (EDV) is the volume of blood in the right and/or left ventricle at the end load or filling in the diastole phase (or the amount of blood in the ventricles just before the systole phase). The end systolic volume (ESV) is the volume of blood in the ventricle at the end of contraction (or the systole phase), and the beginning of filling (or diastole). The end systolic volume is the lowest volume of blood in the ventricle at any point in the cardiac cycle. The main factors that affect the end systolic volume are afterload and the contractility of the heart.

Referring to the embodiment as depicted in FIG. 4A, the following is the manner for correlating the RR-interval 312 and ventricular blood volume. The beginning of the RR-interval 312 is the crest of the R-wave 306 also called the R-wave crest, as depicted in FIG. 3. The beginning of the RR-interval 312 may be correlated to a period of the peak blood volume 314 (for the left ventricular end-diastolic volume or LVEDV) corresponding to a period (time duration) of isovolumetric contraction (IC). The ST-T segment 324 (also called, the ST-T duration) may be correlated to a period of minimum blood volume (the left ventricular end systolic volume or LVESV) corresponding to a period (duration) of isovolumetric relaxation (IR). During left ventricular end-diastolic volume (LVEDV) and left ventricular end systolic volume (LVESV), the heart is in a period of standstill (relaxation or relative standstill). Applying (emitting) an amount of energy (radio-frequency energy), via the puncture device 102 (as depicted in FIG. 1) while the heart is in a period of standstill (relaxation) means the force of the tissue (the outer surface of the heart) being pushed against (acting on) the puncture device 102 is relatively stable (that is, not increasing or not decreasing in magnitude of tissue force applied by the heart tissue).

Referring to the embodiment as depicted in FIG. 4B, tenting the ventricle (of the heart) during the systole phase may result in over-application of force received from (imparted by) the puncture device 102 to the outer surface of the heart, during the diastole phase (when the ventricles fill with blood). Applying (emitting) the energy (radio-frequency energy) while the tissue force acting on the puncture device 102 (as depicted in FIG. 1) is relatively higher may result, disadvantageously, in inadvertent (accidental) puncturing of (into) the myocardium and/or the ventricle (tissue located or positioned adjacent to the pericardium layer that was punctured by the puncture device 102), for which case this may lead to adverse (unwanted) medical complications for the patient. Timing for the application (emission) of energy (radio-frequency energy) from the puncture device 102 to the pericardium layer may reduce (at least in part), or preferably eliminate, the risk of puncturing the tissue directly beneath (adjacent to) the pericardium layer. The myocardium layer is the muscle layer of the heart, and is made up of cardiomyocytes, and is found in the walls of all four chambers of the heart (though it is thicker in the ventricles and thinner in the atria). The pericardium layer is the fibrous sac that surrounds the heart (the myocardium). The pericardium layer may be divided into three layers: the fibrous pericardium, the parietal pericardium and the visceral pericardium (that is, the inner surface of the fibrous pericardium is lined by the outer or parietal layer of serous pericardium).

Figure 5:
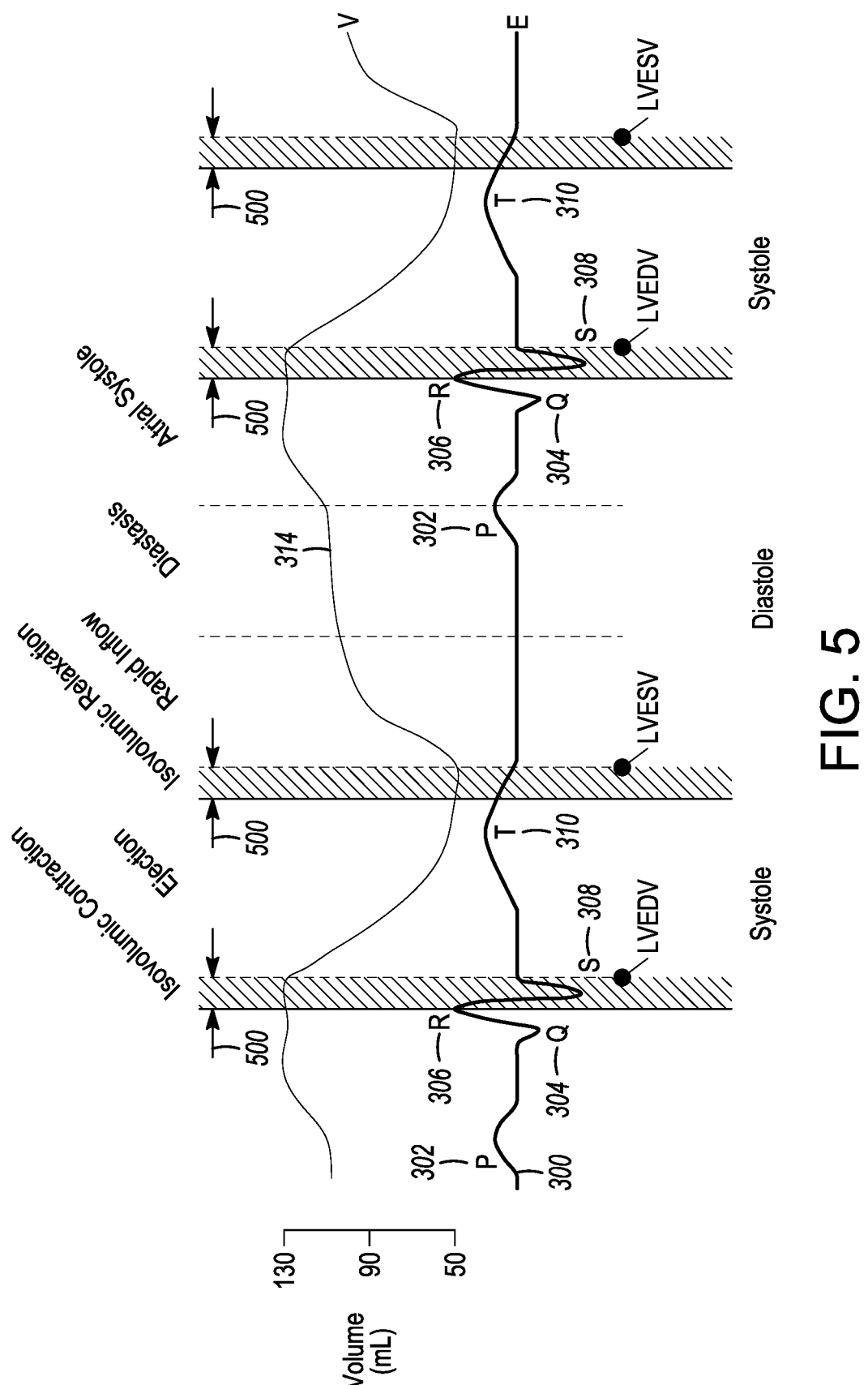
FIG. 5 depicts a schematic view of an embodiment of an electrocardiogram tracing, which may be used by the puncture device of FIG. 1 (for puncturing the pericardium layer of the heart)

FIG. 5 depicts a schematic view of an embodiment of an electrocardiogram tracing 300, which may be used by the puncture device 102 of FIG. 1 (for puncturing the pericardium layer of the heart).

Referring to the embodiment as depicted in FIG. 5, there is depicted a treatment time duration 500 (also called an optimal period). The treatment time duration 500 is configured to span a part of the electrocardiogram tracing 300. The treatment time duration 500 is a duration of time, during which the application (emission) of energy (radio-frequency energy) to the pericardium layer forms the puncture through the pericardium layer (preferably, over the ventricles of the heart, etc.). The treatment time duration 500 is performed during isovolumetric contraction (IC), and may be called an isovolumetric-contraction duration. During treatment time duration 500, the heart is in a natural state of (relative) stand-still during isovolumetric contraction (left ventricular end-diastolic volume or LVEDV) or isovolumetric relaxation (left ventricular end systolic volume or LVESV). The duration of application (emission) of energy (radio-frequency energy) occurs when (while) the force applied by the outer surface of the heart against the distal tip of the puncture device 102 is relatively stable. The crest of the R-wave 306 (the R-wave crest), which indicates the start of isovolumetric contraction (IC), may be easier to detect than delineating the period of isovolumetric relaxation (IR) occurring between the crest of the T-wave 310 and the end of the T-wave 310.

Referring to the embodiment as depicted in FIG. 5, the treatment time duration 500 spans, at least in part, isovolumetric contraction (IC). During treatment time duration 500, the heart is in a state of relative stand-still during isovolumetric contraction.

Referring to the embodiment as depicted in FIG. 5, during the treatment time duration 500, the pericardium layer is punctured after a crest of the R-wave 306 indicates the start of isovolumetric contraction (IC).

Referring to the embodiment as depicted in FIG. 5, in accordance with an embodiment, to help reduce unwanted movement of the puncture device 102 during puncturing (of the pericardium layer), the puncture device 102 contacts (or is positioned proximate to) the pericardium layer (that is, the target tissue to receive treatment) and the puncture device 102 is activated (to emit energy) for puncturing the pericardium layer during a state of heart stasis (in which there is a slowing, or a stoppage, of the normal flow of blood circulating through the heart). This arrangement reduces (preferably, removes) changes in contact force between the distal tip of the puncture device 102 and the pericardium layer while the puncture device 102 is activated (used to emit energy) to puncture the pericardium layer.

Referring to the embodiment as depicted in FIG. 5, in accordance with an embodiment, as the contact force is removed (removed before the end of) the RR-interval 312, a mechanical switch (known and not depicted) is configured to break an electrical connection, thereby preventing emission of energy (from the puncture device 102) for the case where the contact force (between the puncture device 102 and the pericardium layer) increases. Two separate electrical connections for the puncture device 102 may be utilized: (A) a first electrical connection for the control of the energy line (wire), and (B) a second electrical connection for the control (collection) of the electrocardiogram signal. For this arrangement, only the energy line may be broken during periods when a relatively higher force might be applied (thereby potentially improving safety). Emitting energy is only possible (recommended) during the RR-interval 312 regardless of ability to filter and/or detect the correct period (such as, the treatment time duration 500) from the electrocardiogram tracing 300. This arrangement might be sensitive to positioning of the puncture device 102 and may be less desirable. It will be appreciated that, generally, emitting energy may be applied anywhere in the R-R interval 312 as the R-R interval 312 contains the whole QRS signal, it can include both the referenced optimal treatment time (puncture time) and non-optimal treatment time or puncture time.

Figure 6:
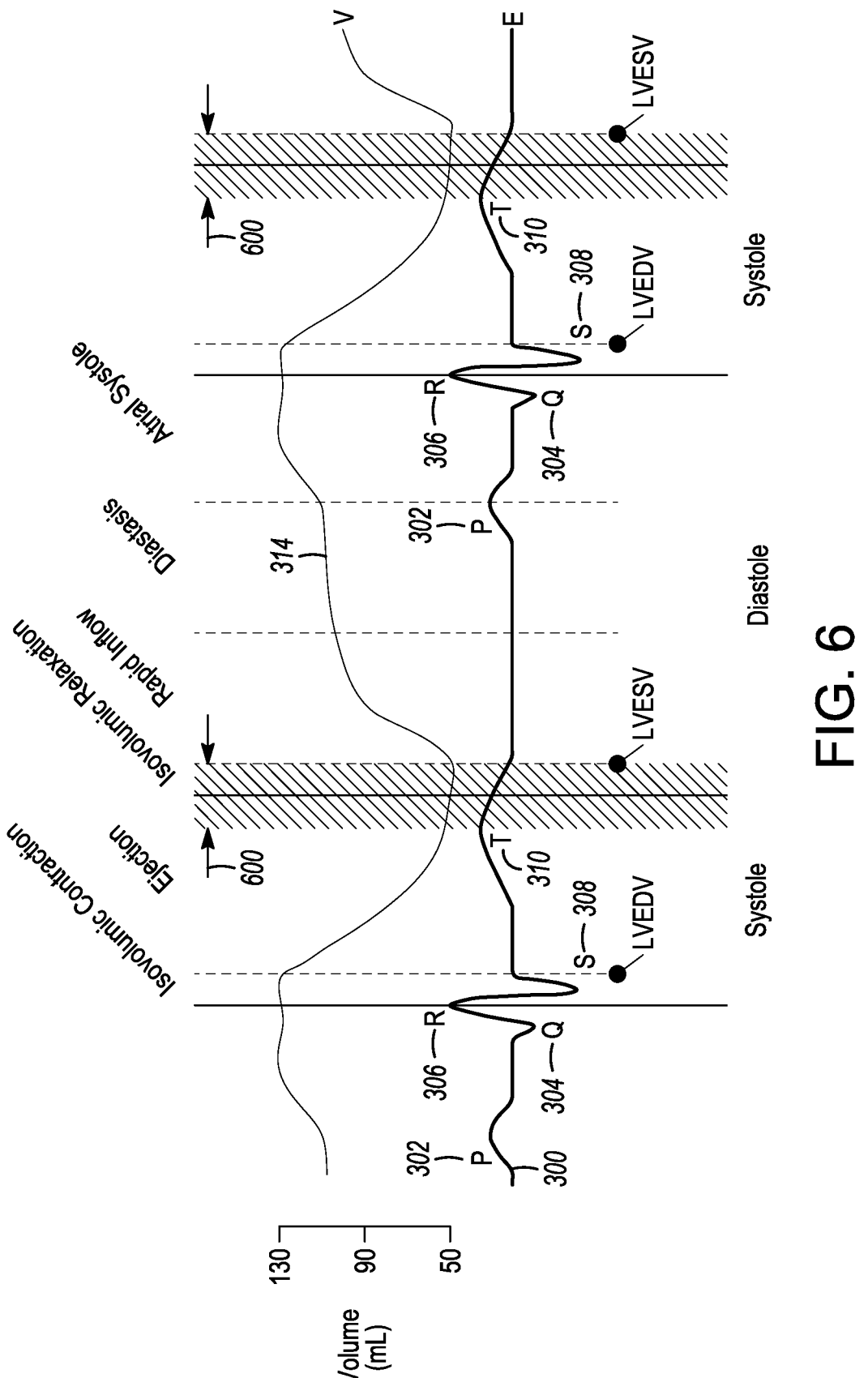
FIG. 6 depicts a schematic view of an embodiment of an electrocardiogram tracing, which may be used by the puncture device of FIG. 1 (for puncturing the pericardium layer of the heart)

FIG. 6 depicts a schematic view of an embodiment of an electrocardiogram tracing 300, which may be used by the puncture device 102 of FIG. 1 (for puncturing the pericardium layer of the heart).

Referring to the embodiment as depicted in FIG. 6, there is depicted a treatment time duration 600 (also called an optimal period) configured to span a part of the electrocardiogram tracing 300. The treatment time duration 600 is configured to span a part of the electrocardiogram tracing 300 (generated from an electrocardiogram signal). The electrocardiogram signal is configured to indicate (provide) a cardiac cycle of the heart (of the patient). During the treatment time duration 600, the pericardium layer (positioned over the ventricles of the heart) is punctured (by emitting energy from the puncture device 102 while the puncture device 102 is positioned proximate to the pericardium layer) during the time duration in which the heart is relatively still (preferably, without inadvertently imparting unwanted damage to the tissue located adjacent to the pericardium layer). During the treatment time duration 600, the pericardium layer (preferably, positioned over the ventricles of the heart) is punctured, preferably without inadvertently imparting damage to the tissue located adjacent to the pericardium layer. Selective emission (delivery) of the energy (radio-frequency energy) during the treatment time duration 600 may result in an acceptable time duration for selective emission of energy from the puncture device 102 without inadvertently imparting damage to the tissue located adjacent to the pericardium layer.

Referring to the embodiment as depicted in FIG. 6, during the treatment time duration 600, the pericardium layer is punctured during the time in which the heart is relatively still.

Referring to the embodiment as depicted in FIG. 6, during the treatment time duration 600, the pericardium layer is punctured during isovolumetric relaxation.

Referring to the embodiment as depicted in FIG. 6, the emission of energy (radio-frequency energy) during the treatment time duration 600 is activated toward the pericardium layer of the heart, thereby forming the puncture (through the pericardium layer) during isovolumetric relaxation (the LVESV period). On the one hand, the LVESV period may be relatively more difficult to detect. But on the other hand, the LVESV period may be beneficial for timing of a duration of the emission of energy from the puncture device 102. Due to the reduction of tissue force experienced by the puncture device 102 (as depicted in FIG. 1 or FIG. 2), the signal crest of the T-wave 310 may (instead) be used to delineate the start of the treatment time duration 600 for the application (emission) of energy from the puncture device 102. Between (A) the crest of the T-wave 310 (also known as the T-wave crest) and (B) the zero amplitude (of the waveform of the electrocardiogram tracing 300), the differential in blood volume is peaking, and, therefore, this condition may take into account a larger period where the heart is in a state of relative relaxation or at near standstill (near relaxation).

Figure 7:
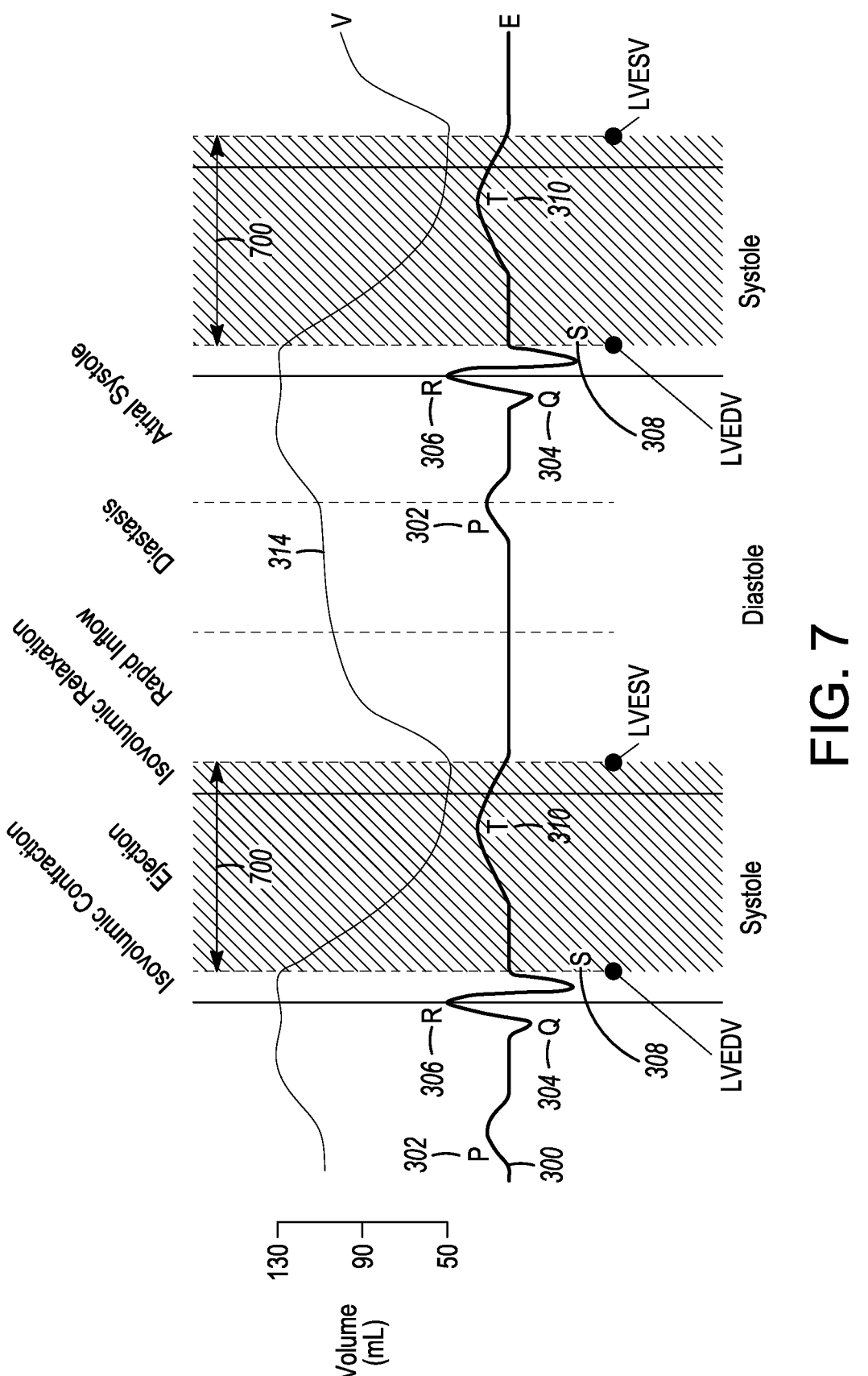
FIG. 7 depicts a schematic view of an embodiment of an electrocardiogram tracing, which may be used by the puncture device of FIG. 1 (for puncturing the pericardium layer of the heart)

FIG. 7 depicts a schematic view of an embodiment of an electrocardiogram tracing 300, which may be used by the puncture device 102 of FIG. 1 (for puncturing the pericardium layer of the heart).

Referring to the embodiment as depicted in FIG. 7, there is depicted a treatment time duration 700 (also called an optimal period) configured to span a part of the electrocardiogram tracing 300. The energy is applied (emitted from the puncture device 102, as depicted in FIG. 1) starting from the beginning of the RR-interval 312 while the blood volume decreases from the left ventricular end-diastolic volume (LVEDV) to the left ventricular end systolic volume (LVESV) (that is, over about 0.4 seconds). The beginning of the RR-interval 312 has the maximum amplitude seen in the electrocardiogram tracing 300, and, therefore, the physician experience (have) a larger degree of confidence when detecting this phase (interval) compared to other phases (intervals). However, to ensure an even greater confidence, in addition to the electrocardiogram tracing 300, a phonocardiogram tracing (PCG tracing) may be analyzed. The phonocardiogram tracing is an equivalent to the electrocardiogram tracing 300. The electrocardiogram tracing 300 is any tracing derived (computed) from any type of signal (electrical signal, acoustic signal, pressure signal, etc.) provided by any suitable transducer and/or sensor. The phonocardiogram tracing is a tracing, a chart or a record of the sounds made by the heart (the sounds may be detected by a microphone transducer, etc.). When the atrioventricular valves close, sound may be observed, and the sound may be more detectable or occurs near the beginning of the RR-interval 312. The beginning of the RR-interval 312 has a maximum amplitude seen in the electrocardiogram tracing 300, and therefore there may be a larger confidence when detecting this phase compared to other phases. Other aspects of the electrocardiogram tracing 300 may be utilized to detect the beginning of the RR-interval 312 (if so desired).

Referring to the embodiment as depicted in FIG. 7, during the treatment time duration 700, the pericardium layer is punctured starting from a beginning of the RR-interval 312 while the blood volume decreases from the left ventricular end-diastolic volume (LVEDV) to the left ventricular end systolic volume (LVESV).

Referring to the embodiment as depicted in FIG. 7, during the treatment time duration 700, the pericardium layer is punctured starting from the ST-T segment 324 during the ejection phase located after the QRS-complex (304, 306, 308).

Referring to the embodiment as depicted in FIG. 7, the puncture device 102 (as depicted in FIG. 1) is configured (preferably) to: (a) sense or detect the beginning of the RR-interval 312 (as depicted in FIG. 3), and (b) selectively emit energy (radio-frequency energy, preferably a pulse of energy) to the pericardium layer (of the heart). This is done in such a way that the energy (that was emitted) facilitates formation of a puncture through the pericardium layer without, preferably, inflicting unwanted damage (as a result of treatment or puncturing) to adjacently located tissues (of the heart). Preferably, the pulse of energy may range, for instance, from about 0.1 seconds to about 0.4 seconds.

Referring to the embodiment as depicted in FIG. 7, the electrocardiogram signal is acquired (by the computer system 200, as depicted in FIG. 1). The electrocardiogram tracing 300 is generated based on the electrocardiogram signal that was acquired. The beginning of the RR-interval 312 is detected (as depicted in FIG. 3, etc.) or is identified in the electrocardiogram tracing 300 (by the computer system 200). To puncture the pericardium layer, the application (emission) of energy from the puncture device 102 may start at the beginning of the RR-interval 312 (that was detected by the computer system 200, as depicted in FIG. 1). It may be possible to apply a similar control strategy for the case where it may be required to perform epicardial or endocardial radio-frequency ablations or pulse-field ablation (to ensure good catheter contact). For the case where the contact force between the radio-frequency ablation catheter and the tissue is too large, steam pops and/or perforation may occur. For the case where the contact force is too small, the lesion size may not be large enough. By applying radio-frequency energy during a specific time interval, the physician may be more confident that an optimal contact force may be achieved. For the case where the contact force between the pulse-field ablation catheter and the tissue is too small, the surface area of contact may be reduced and resulting lesion may not be successful. By applying pulse-field ablation energy during a specific time interval, the physician may be more confident that an optimal contact force and resulting lesion may be achieved. It will be appreciated that, generally radio-frequency ablation treatment times can take a few seconds to complete a lesion, and may take longer than the intervals noted here, and/or may only be applicable to pulse-field ablation treatment times (short duration for treatment).

Referring to the embodiment as depicted in FIG. 7, the ST-T segment 324 (also called the ST-T interval) occurs during the ejection phase positioned or located after the QRS-complex (304, 306, 308). Similar to the embodiment of FIG. 6, the application (emission) of energy (radio-frequency energy) during the ST-T segment 324 may be advantageous as the tissue force (application force) acting on the puncture device 102 (as depicted in FIG. 1 or FIG. 2) is continuously decreasing. The treatment time duration 700 may be easier to detect for the timing (application) of energy (radio-frequency energy) during the treatment time duration 600 (as depicted in FIG. 6) associated with the crest of the T-wave 310 (as depicted in FIG. 6). The treatment time duration 700 may be easier to detect and time the application of radio-frequency energy to than the treatment time duration 500 (as depicted in FIG. 5) associated with the LVESV period (as depicted in FIG. 5).

Figure 8:
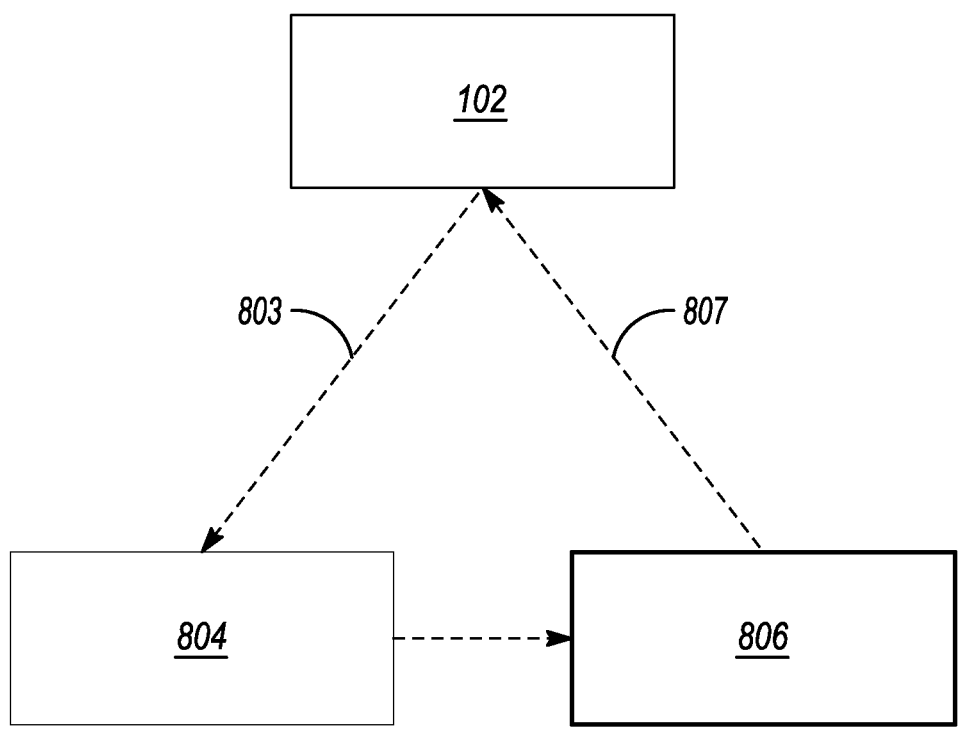
FIG. 8 depicts a schematic view of interactions between the puncture device (as depicted in FIG. 1), an electrophysiology recording equipment and a radio-frequency generator (for use with the puncture device)

FIG. 8 depicts a schematic view of interactions between the puncture device 102 (as depicted in FIG. 1), an electrophysiology recording equipment 804 (EP recording system) and a radio-frequency generator 806 (for use with the puncture device 102).

Referring to the embodiment as depicted in FIG. 8, there is depicted an embodiment of interactions (cooperation) between the puncture device 102 (as depicted in FIG. 1), an electrophysiology recording equipment 804 and a radio-frequency generator 806 (for use with the puncture device 102). The electrophysiology recording equipment 804 and the radio-frequency generator 806 (or energy generator) are known to persons skilled in the art, and are not described in any specific detail). The puncture device 102 (as depicted in FIG. 1 or FIG. 2) is configured to acquire (receive) the electrocardiogram signal 803. The electrophysiology recording equipment 804 is configured to process the electrocardiogram signal 803. The electrocardiogram signal 803 is configured to indicate (provide) the cardiac cycle of the heart, of the patient. The electrophysiology recording equipment 804 is also configured to identify (preferably) the beginning of the RR-interval 312 based on the electrocardiogram signal 803 (that was received or detected). The radio-frequency generator 806 is configured to apply (emit) the radio-frequency energy 807 at the beginning of the RR-interval 312 (this is done after the puncture device 102 is positioned proximate to the pericardium layer). For instance, the electrophysiology recording equipment 804 (also called a data-acquisition system) may include the BIONOMADIX (TRADEMARK) 2 CHANNEL WIRELESS ECG transmitter (manufactured by BIOPAC SYSTEMS INC. (headquartered in U.S.A.). For instance, the electrophysiology recording equipment 804 may include the CARDIOLAB (TRADEMARK) system manufactured by GE HEALTHCARE COMPANY (headquartered in U.S.A.).

The electrophysiology recording equipment 804 is (preferably) configured to: (a) receive the electrocardiogram signal 803 from an electrocardiographic sensor (mounted to a distal portion of the puncture device 102, etc.), and (b) process the electrocardiogram signal that was received (including, preferably, removal of noise signals, subtraction of background signals, delineation of the waves identified in the electrocardiogram tracing 300, etc.) and/or (c) identify the treatment time duration (500, 600, 700, 1000) (as depicted in FIG. 5, FIG. 6, FIG. 7, and FIG. 10) from the electrocardiogram tracing 300. The treatment time duration is configured to span a part of (to be identified in) the electrocardiogram tracing 300 of the cardiac cycle (of the heart), such as the beginning of the RR-interval 312, etc.

Referring to the embodiment as depicted in FIG. 8, during the treatment time duration 1000, the pericardium layer is punctured starting from a crest of the R-wave 306 indicating a start of isovolumetric contraction (IC).

Referring to the embodiment as depicted in FIG. 8, connector cables are configured to facilitate communication between the puncture device 102, the radio-frequency generator 806 and the data acquisition system (that is, the electrophysiology recording equipment 804). The radio-frequency generator 806 is configured to receive an indication signal from the data-acquisition system, in which the indication signal is configured to indicate (provide) the beginning of the RR-interval 312. The radio-frequency generator 806 is configured to selectively apply (emit) energy (radio-frequency energy) once the indication signal is received from the data acquisition system (the electrophysiology recording equipment 804), in which the indication signal is configured to indicate (provide) the beginning of the RR-interval 312. The radio-frequency generator 806 is (preferably) configured to allow (suggest) that the operator (user) selectively apply radio-frequency energy once the beginning of the RR-interval 312 is identified (by the computer system 200 as depicted in FIG. 1). The radio-frequency generator 806 is also configured to automatically apply radio-frequency energy once (after) the beginning of the RR-interval 312 is detected. The radio-frequency generator 806 may be configured to allow or suggest that the operator apply (selectively emit) energy. The radio-frequency generator 806 may be configured to urge the puncture device 102 to automatically apply (emit) energy once the beginning of the RR-interval 312 is detected, etc. The radio-frequency generator 806 may be configured to facilitate communication between the puncture device 102, the radio-frequency generator 806 and the electrophysiology recording equipment 804.

Referring to the embodiment as depicted in FIG. 8, to summarize, the electrocardiogram signal 803 may be acquired when (while) the puncture device 102 is being used to tent the pericardium layer. The electrocardiogram signal 803 may be processed, etc. (for enhancement of the signal). When the beginning of the RR-interval 312 (as depicted in FIG. 3) is identified, energy may be applied (emitted) from the puncture device 102. During the RR-interval 312, the volume of blood decreases, and therefore, the contact force between the puncture device 102 and the pericardium layer may also decrease. This is a safer option than puncturing when the contact force increases over time, which may lead to accidental puncturing of the tissue located adjacent to the pericardium layer.

Figure 9:
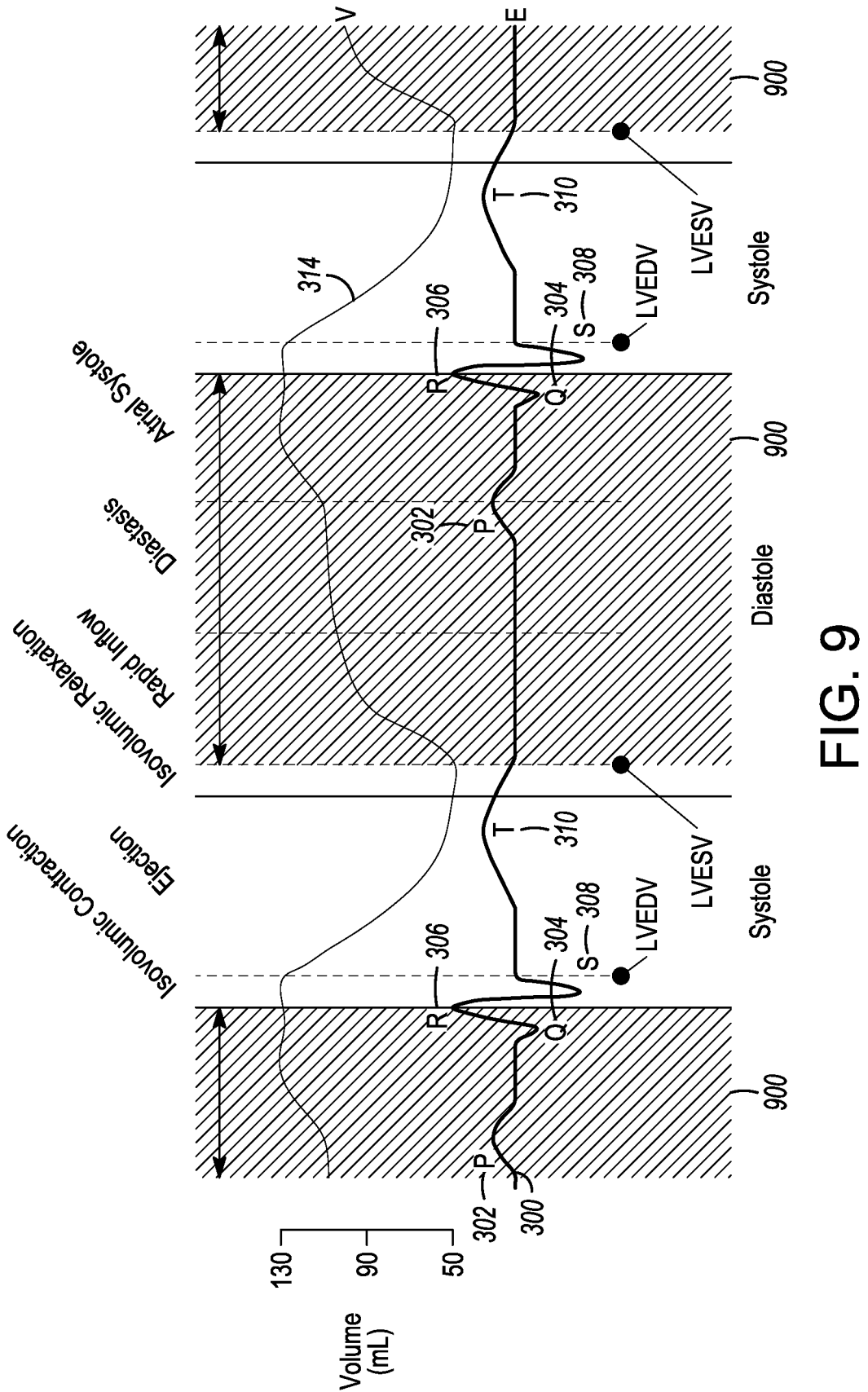
FIG. 9 depicts a schematic view of an embodiment of an electrocardiogram tracing, which is not to be used by the puncture device of FIG. 1 (for puncturing the pericardium layer of the heart)

FIG. 9 depicts a schematic view of an embodiment of an electrocardiogram tracing 300 of a cardiac cycle (of the heart), which is not to be used by the puncture device 102 of FIG. 1.

Referring to the embodiment as depicted in FIG. 9, there is depicted a treatment time duration 900 (a non-optimal time period) for not applying (emitting) energy (radio-frequency energy) from the puncture device 102 (as depicted in FIG. 1) for the formation of the puncture through the pericardium layer. The TR-interval 334 (as depicted in FIG. 3, also called the TR-interval period) and the TP-interval 320 (TP-interval period) (the TP-PR interval is a combination of the TR-interval 334 and the TP-interval 320) occur during rapid inflow, the diastasis phase and the atrial systole phase. During these phases, pressure against the distal tip of the puncture device 102 from the tissue may increase. As radio-frequency puncture does not need an appreciable application of force to puncture the tissue, this case may increase the risk of inadvertent puncturing of the underlying myocardium layer (of the heart) in response to excessive application of force by the heart against the puncture device 102 (resulting from increased blood pressure within the heart).

Referring to the embodiment as depicted in FIG. 9, a non-optimal time period for not puncturing the pericardium layer is the TR-interval 334 and the TP-interval 320 during rapid inflow associated with the diastasis phase and the atrial systole phase of the heart.

Figure 10:
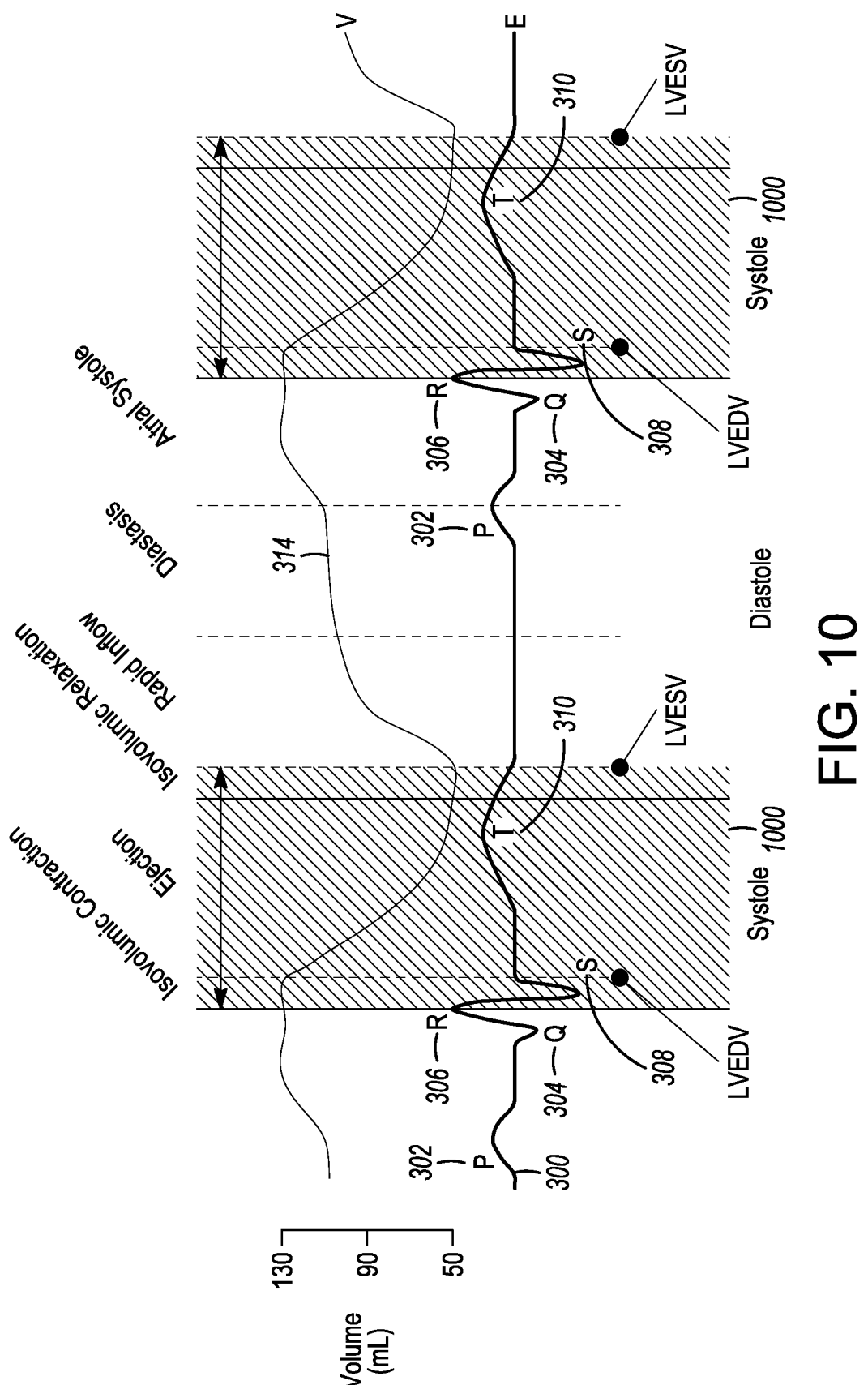
FIG. 10 depicts a schematic view of an embodiment of an electrocardiogram tracing, which may be used by the puncture device of FIG. 1 (for puncturing the pericardium layer of the heart)

FIG. 10 depicts a schematic view of an embodiment of an electrocardiogram tracing 300, which may be used by the puncture device 102 of FIG. 1 (for puncturing the pericardium layer of the heart).

Referring to the embodiment as depicted in FIG. 10, there is depicted a treatment time duration 1000 (also called an optimal period) configured to span a part of the electrocardiogram tracing 300. The treatment time duration 1000 (optimal period) is configured to indicate (provide) an acceptable time for the application (emission) of energy (radio-frequency energy) from the puncture device 102 for the formation of the puncture through the pericardium layer. Similar to the treatment time duration 500 (as depicted in FIG. 5) and/or the treatment time duration 700 (as depicted in FIG. 7), the crest of the R-wave 306 (the R-wave crest, which is the start of the RR-interval 312) indicates the start of isovolumetric contraction (IC), which may be used. The crest of the R-wave 306 may be relatively easier to detect than other time periods or time durations. For the case where the patient has an abnormal instance of the electrocardiogram tracing 300, the R-wave 306 may be a relatively easier time period to start and stop the application (emission) of energy (radio-frequency energy) due to the large change in signal in comparison to the rest of the cardiac cycle of the heart.

Figure 11:
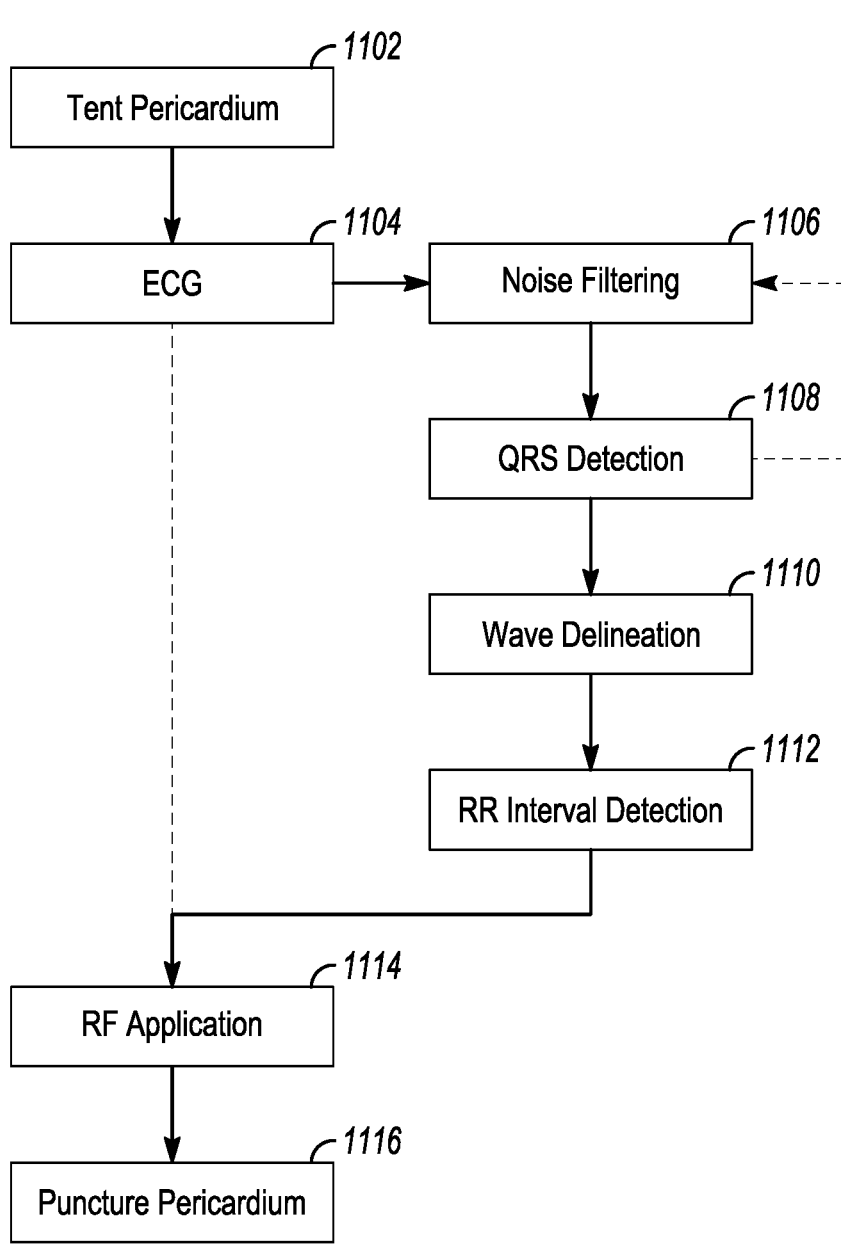
FIG. 11 depicts a flowchart view of an embodiment of a workflow for using the puncture device of FIG. 1.

FIG. 11 depicts a flowchart view of an embodiment of a workflow (method) for using the puncture device 102 (as depicted in FIG. 1).

Referring to the embodiment as depicted in FIG. 11, there is depicted an embodiment of a workflow for utilizing the puncture device 102 (as depicted in FIG. 1). The workflow (method) as depicted in FIG. 11 includes step 1102 to step 1116.

Referring to the embodiment as depicted in FIG. 11, step 1102 includes (preferably) tenting the pericardium layer; the puncture device 102 is physically maneuvered (moved) into the pericardium layer. This is done in such a way that the puncture device 102 urges the pericardium layer to become tented (temporarily deformed).

Referring to the embodiment as depicted in FIG. 11, step 1104 includes processing (receiving) the electrocardiogram sensor (that was received from the electrocardiogram sensor), in which the electrocardiogram sensor is to be used for generating the electrocardiogram tracing 300 (as depicted in FIG. 3). Step 1104 is done while the puncture device 102 physically tents the pericardium layer. During step 1104, the computer system 200 (as depicted in FIG. 1) receives the electrocardiogram signal, from the electrocardiographic sensor, in which the electrocardiogram signal indicates the cardiac cycle of the heart. The computer system 200 generates the electrocardiogram tracing 300 based on the electrocardiogram signal that was received from the electrocardiographic sensor (preferably, the electrocardiographic sensor is mounted on the distal tip of the puncture device 102, etc.).

Referring to the embodiment as depicted in FIG. 11, step 1106 includes (preferably) reducing (preferably, removing) noise from the electrocardiogram signal (before generating the electrocardiogram tracing 300). Step 1106 is done while the puncture device 102 physically tents the pericardium layer.

Referring to the embodiment as depicted in FIG. 11, step 1108 includes (preferably) detecting the QRS-complex (304, 306, 308), as depicted in FIG. 3, to be found or identified in the electrocardiogram tracing 300. Step 1108 is done while the puncture device 102 physically tents the pericardium layer.

Referring to the embodiment as depicted in FIG. 11, step 1110 includes analysis (delineation, segmentation) of the components of the electrocardiogram tracing 300. Step 1110 is done while the puncture device 102 physically tents the pericardium layer. During step 1110, the computer system 200 identifies the treatment time duration (500, 600, 700, 1000), as depicted in FIG. 5, FIG. 6, FIG. 7, and FIG. 10. The treatment time duration (500, 600, 700, 1000) is configured to span a part of the electrocardiogram tracing 300 that was generated. The tissue (such as the pericardium layer) is puncturable during, at least in part, the treatment time duration (500, 600, 700, 1000). This is done in such a way that, during, at least in part, the treatment time duration (500, 600, 700, 1000), the blood pressure within the heart urges the pericardium layer to impart a relatively lower amount of tissue force toward the puncture device 102 while the puncture device 102 is positioned proximate to the pericardium layer and, the puncture device 102 is activated to puncture the pericardium layer. The computer system 200 provides the treatment time duration (500, 600, 700, 1000) that was identified (whereby inadvertent damage to the tissue located adjacent to the pericardium layer is reduced (preferably avoided) while the pericardium layer is punctured during the treatment time duration (500, 600, 700, 1000).

Referring to the embodiment as depicted in FIG. 11, step 1112 includes (preferably) identifying the RR-interval 312 (as depicted in FIG. 3) from the components of the electrocardiogram tracing 300 (that were analyzed). Step 1112 is done while the puncture device 102 physically tents the pericardium layer. During step 1112, the computer system 200 provides the treatment time duration (500, 600, 700, 1000) to the energy generator 118 (as depicted in FIG. 1), and the energy generator 118 selectively sends a pulse of energy to the puncture device 102 in accordance with the electrocardiogram tracing 300 (that was received from the computer system 200).

Referring to the embodiment as depicted in FIG. 11, step 1114 includes activating the puncture device 102 (as depicted in FIG. 1) in such a way that energy (such as, radio-frequency energy) is selectively emitted from the puncture device 102. Step 1114 is done while the puncture device 102 physically tents the pericardium layer.

Referring to the embodiment as depicted in FIG. 11, step 1116 includes puncturing the tissue (the pericardium layer of the heart). Step 1116 is done while the puncture device 102 physically tents the pericardium layer.

FIG. 12A, FIG. 12B, FIG. 12C and FIG. 12D depict schematic views of the heart during various steps of the workflow in connection with FIG. 11.

Figure 12A:
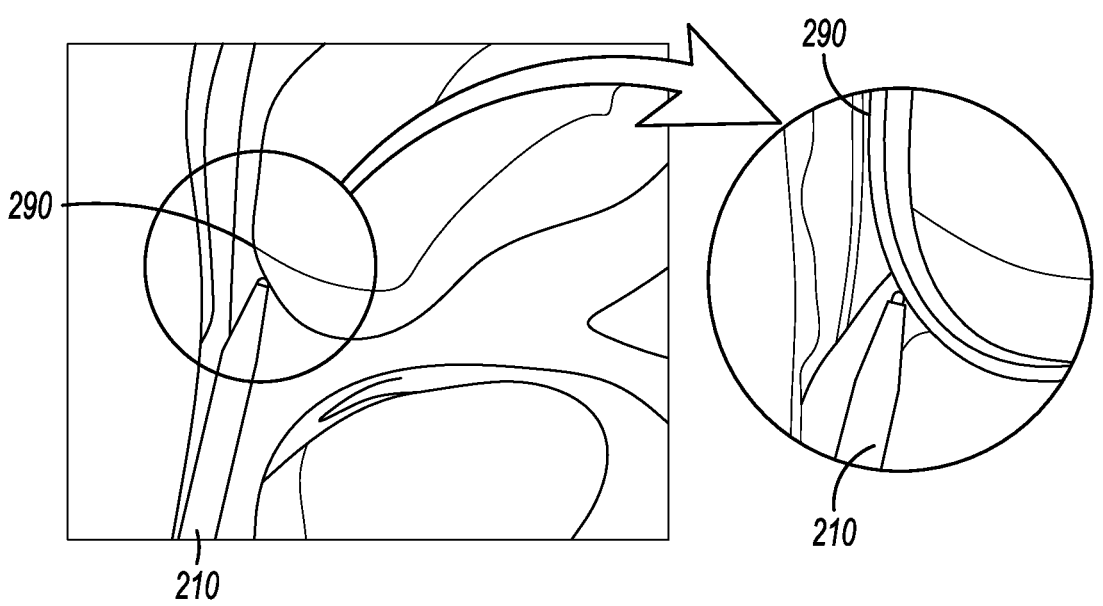
FIG. 12A, FIG. 12B, FIG. 12C and FIG. 12D depict schematic views of the heart during various steps of the workflow in connection with FIG. 11.

Referring to the embodiment as depicted in FIG. 12A, it will be appreciated that (if desired), a stylet (known and not depicted) is initially used in the introducer 210. The stylet is (then) exchanged for the puncture device 102, and the workflow may continue. For the case where the puncture device 102 is very stiff (such as, with a radio-frequency emitting device), it may be possible to omit the stylet. For the case where the puncture device 102 has sufficient stiffness, it is possible to forgo usage of the introducer 210. The puncture device 102 is placed (positioned) inside an introducer 210 (at the distal portion of the introducer 210). The puncture device 102 and the introducer 210 are advanced until they reach the pericardium layer 290 (also called the pericardial sac).

Figure 12B:
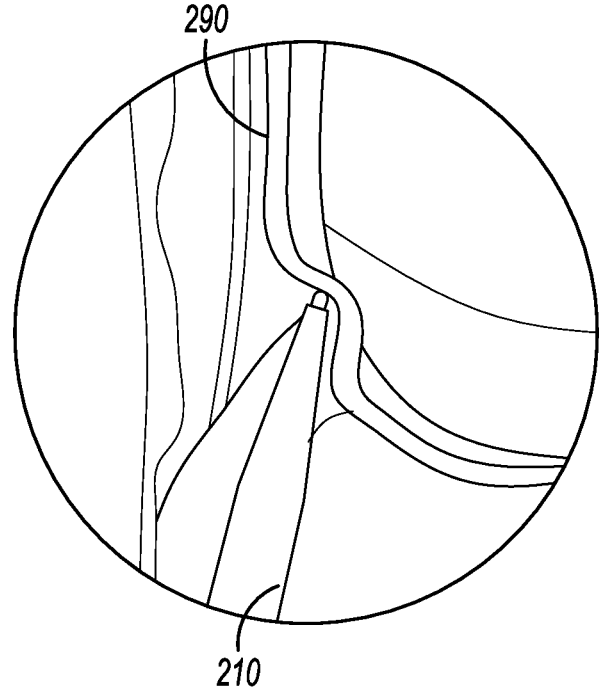

Referring to the embodiment as depicted in FIG. 12B, the puncture device 102 is extended from the interior of the introducer 210 (via the distal end of the introducer 210). This is done in such a way that the puncture device 102 is used (pushed or moved) to tent the pericardium layer 290 of the heart. The computer system 200 is configured to receive the electrocardiogram signal (from the electrocardiogram sensor). If required, the electrocardiogram signal may be filtered (to remove or reduce any noise signal that is included with the electrocardiogram signal).

Figure 12C:
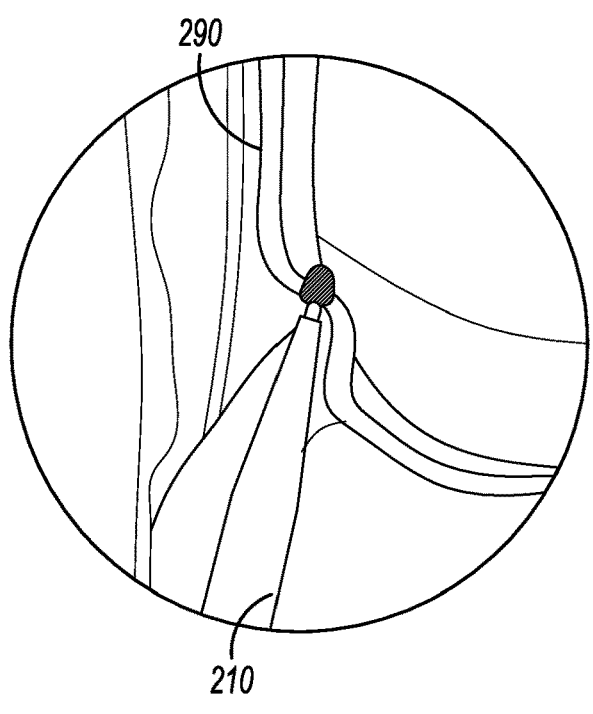

Referring to the embodiment as depicted in FIG. 12C, the electrocardiogram tracing 300 is generated (and is based on the electrocardiogram signal that was received). The computer system 200 (as depicted in FIG. 1) identifies (computes, calculates) a treatment time duration (500, 600, 700, 1000), as depicted, for instance, in FIG. 5, FIG. 6, FIG. 7 and FIG. 10. The treatment time duration (500, 600, 700, 1000) spans a part of (is identified in) the electrocardiogram tracing 300 that was generated. In accordance with a preferred embodiment, the treatment time duration (500, 600, 700, 1000) may include the RR-interval 312 (as depicted in FIG. 3). The pericardium layer is puncturable during, at least in part, the treatment time duration (500, 600, 700, 1000) so that inadvertent damage to the tissue located adjacent to the pericardium layer is reduced (preferably avoided) while the pericardium layer is punctured during the treatment time duration (500, 600, 700, 1000). It will be appreciated that the emission of energy from the puncture device 102 may be allowed, suggested, or automatically executed by the computer system 200. The computer system 200 may directly control the puncture device 102 for activation of energy from the puncture device 102.

Figure 12D:
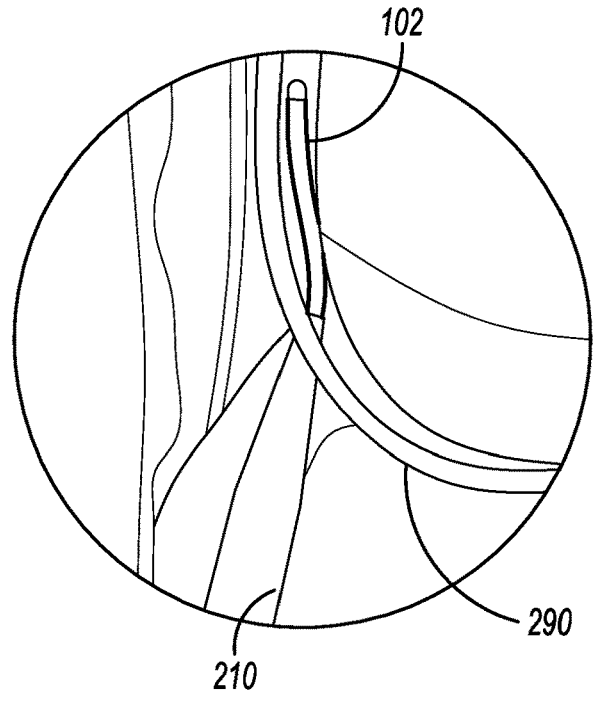

Referring to the embodiment as depicted in FIG. 12D, in accordance with a preferred embodiment, the emission of energy (from the puncture device 102) terminates (ends) before the end of LVESV (the left ventricular end systolic volume).

Figure 13:
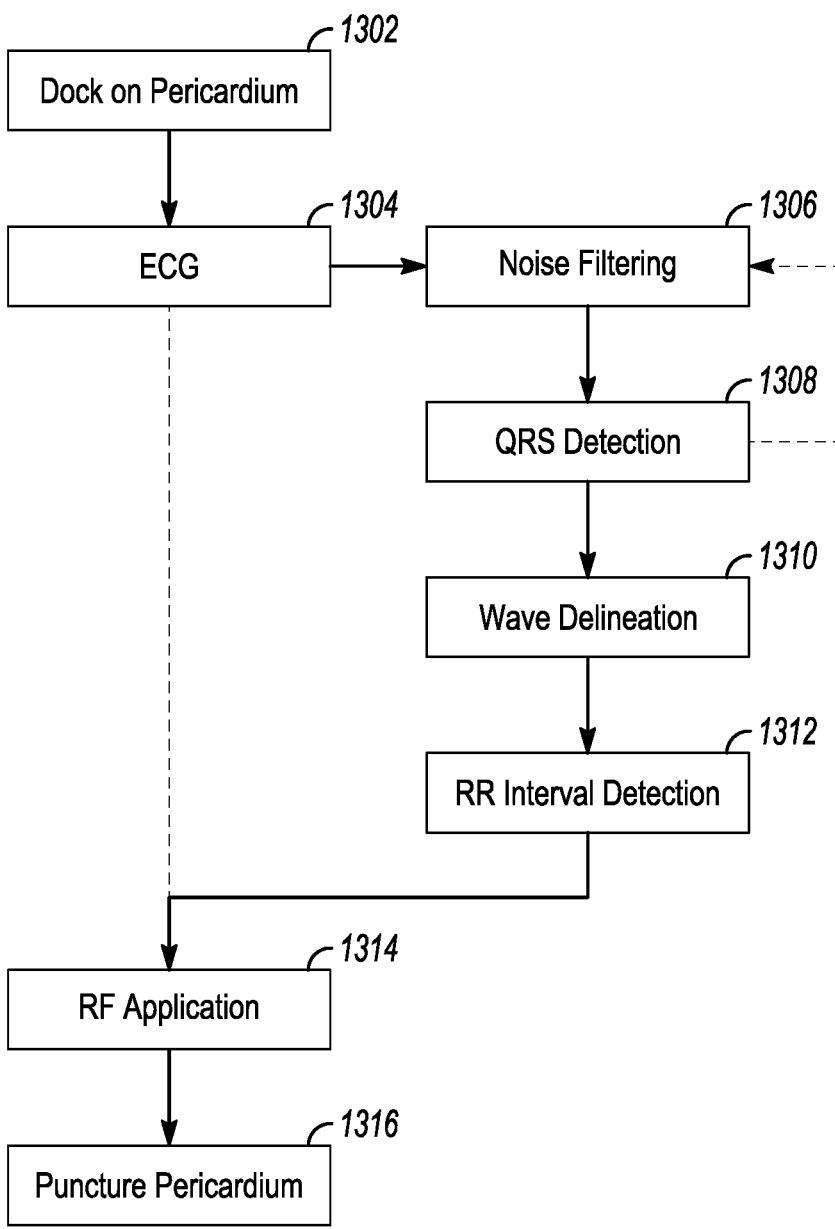
FIG. 13 depicts a flowchart view of an embodiment of a workflow for using the puncture device of FIG. 1.

FIG. 13 depicts a flowchart view of an embodiment of a workflow for using the puncture device 102 (as depicted in FIG. 1). The workflow (method) as depicted in FIG. 13 includes step 1302, step 1304, step 1306, step 1308, step 1310, step 1312, step 1314 and step 1316.

Referring to the embodiment as depicted in FIG. 13, step 1302 includes (preferably) physically maneuvering (moving) the puncture device 102 toward the pericardium layer. This is done in such a way that the puncture device 102 becomes docked on (prolapsed against) the outer surface of the pericardium layer (preferably without tenting the pericardium layer directly into non-target tissue, in sharp contrast to step 1102 of FIG. 11). Step 1304 to step 1316 are similar to step 1104 to step 1116 (as depicted in FIG. 11), respectively.

Referring to the embodiment as depicted in FIG. 13, the distal portion of the puncture device 102 (as depicted in FIG. 1) is configured to dock on (prolapsed against) the surface of the pericardium layer. In accordance with a preferred embodiment, the RR-interval 312 (as depicted in FIG. 3) is then detected. The energy (radio-frequency energy) is emitted (applied) to puncture the pericardium layer (preferably without causing inadvertent damage to adjacently located tissue of the heart, etc.). Rather than tenting the pericardium layer of the heart directly into non-target tissue, the puncture device 102 may be docked on (prolapsed against) the surface of the pericardium layer. After the energy (radio-frequency energy) is emitted (applied), the pericardium layer may prolapse into the pericardial space. The method of using the electrocardiogram tracing 300 and the electrocardiogram signal (to facilitate timing of the puncture) may be similar to the workflow associated with FIG. 11.

FIG. 14A, FIG. 14B, FIG. 14C and FIG. 14D depict schematic views of the pericardium layer of the heart during various steps of the workflow in connection with FIG. 13.

Figure 14A:
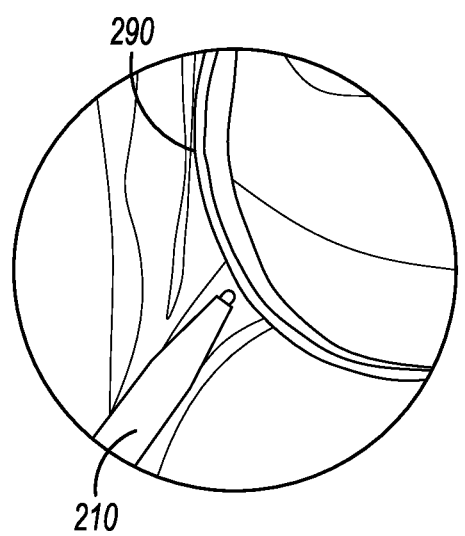
FIG. 14A, FIG. 14B, FIG. 14C and FIG. 14D depict schematic views of the pericardium layer of the heart during various steps of the workflow in connection with FIG. 13.

Referring to the embodiment as depicted in FIG. 14A, a distal portion of an introducer 210 is positioned apposed to the pericardium layer 290. The distal portion of the introducer 210 is docked on (preferably prolapsed against) the surface of the pericardium layer 290 (imposing relatively little force, to the pericardium layer 290).

Figure 14B:
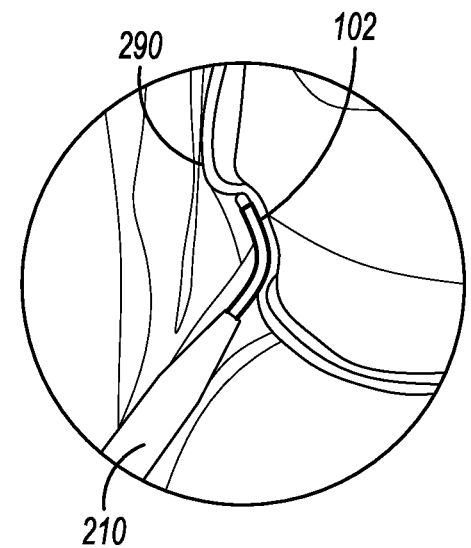

Referring to the embodiment as depicted in FIG. 14B, the puncture device 102 is extended from the interior of the introducer 210 (via the distal end of the introducer 210). The electrocardiogram signal is received (from the electrocardiogram sensor). If required, the electrocardiogram signal may be filtered (to remove or reduce any noise signal that is included with the electrocardiogram signal.

Figure 14C:
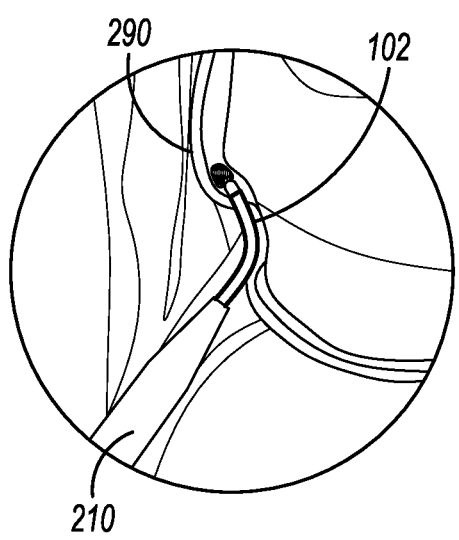

Referring to the embodiment as depicted in FIG. 14C, the electrocardiogram tracing 300 is generated (based on the electrocardiogram signal that was received). The computer system 200 (as depicted in FIG. 1) identifies (computes, calculates) a treatment time duration (500, 600, 700, 1000), as depicted, for instance, in FIG. 5, FIG. 6, FIG. 7 and FIG. 10. The treatment time duration (500, 600, 700, 1000) spans a part of (is identified in) the electrocardiogram tracing 300 that was generated. In accordance with a preferred embodiment, the treatment time duration (500, 600, 700, 1000) may include the RR-interval 312 (as depicted in FIG. 3). The pericardium layer is puncturable during, at least in part, the treatment time duration (500, 600, 700, 1000) so that inadvertent damage to the tissue located adjacent to the pericardium layer is reduced (preferably avoided) while the pericardium layer is punctured during the treatment time duration (500, 600, 700, 1000). It will be appreciated that the emission of energy from the puncture device 102 may be allowed, suggested, or automatically executed by the computer system 200. The computer system 200 may directly control the puncture device 102 for activation of energy from the puncture device 102.

Figure 14D:
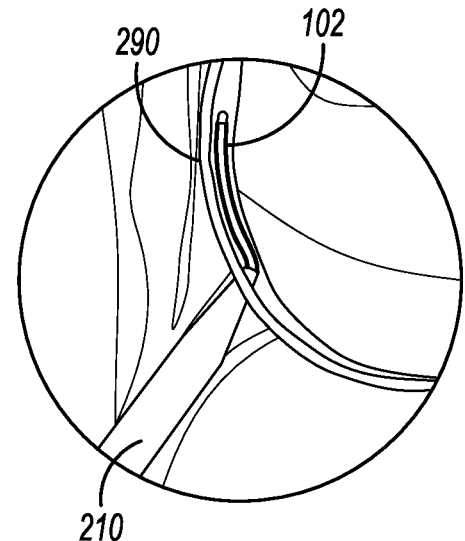

Referring to the embodiment as depicted in FIG. 14D, in accordance with a preferred embodiment, the emission of energy (from the puncture device 102) ends, preferably, before the start of the left ventricular end systolic volume (LVESV).

Figure 15A:
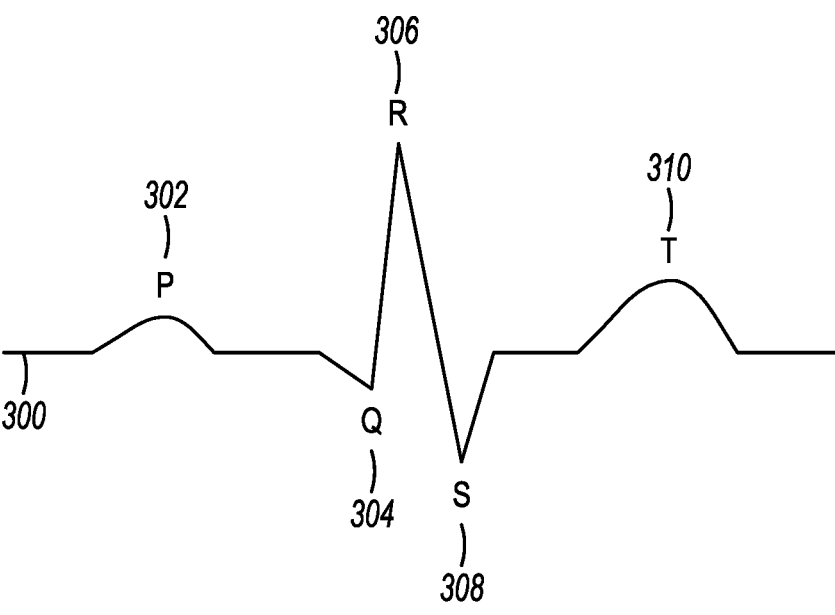
FIG. 15A and FIG. 15B depict schematic representations (views) of embodiments of the electrocardiogram tracings associated with FIG. 7 or FIG. 10.
Figure 15B:
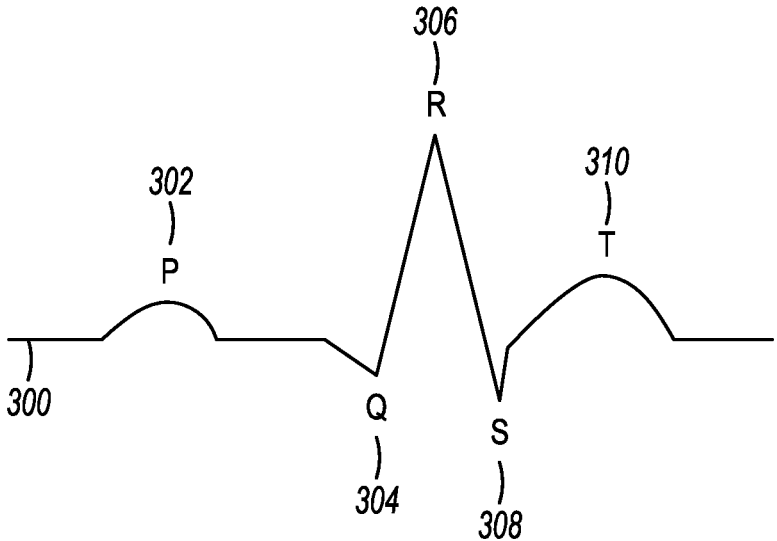

FIG. 15A and FIG. 15B depict schematic representations (views) of embodiments of the electrocardiogram tracing 300 associated with FIG. 7 or FIG. 10.

Referring to the embodiment as depicted in FIG. 15A, there is depicted an embodiment of a normal signal of the electrocardiogram tracing 300 for a normal heart or a healthy heart.

Referring to the embodiment as depicted in FIG. 15B, there is depicted an embodiment of an abnormal signal of the electrocardiogram tracing 300 for a diseased heart.

Referring to the embodiments as depicted in FIG. 15A and FIG. 15B, these signals may affect the efficacy of the computer system 200 (as depicted in FIG. 1, also called a signal analyzer) to detect an optimal period for the application (emission) of energy (such as, radio-frequency energy) in view of the electrical-conduction issues that may be associated with various disease states of the heart. For instance, for the case where it may be desired to detect the ST-T segment 324 (as described for the embodiment of FIG. 7), the difference in amplitude of the signal between (A) the normal signal (as depicted in FIG. 15A) and (B) the abnormal signal (as depicted in FIG. 15B), which may make the start of the ST-segment 322 relatively difficult to detect. As such, detection of when the heart, in general, is in a less vulnerable state may be beneficial, in which a relatively higher confidence may be achieved such as a general application period that includes both isovolumetric contraction (IC) and ejection stages (as described for the embodiment of FIG. 10).

The following is offered as further description of the embodiments, in which any one or more of any technical feature (described in the detailed description, the summary and the claims) may be combinable with any other one or more of any technical feature (described in the detailed description, the summary and the claims). It is understood that each claim in the claims section is an open ended claim unless stated otherwise. Unless otherwise specified, relational terms used in these specifications should be construed to include certain tolerances that the person skilled in the art would recognize as providing equivalent functionality. By way of example, the term perpendicular is not necessarily limited to 90.0 degrees, and may include a variation thereof that the person skilled in the art would recognize as providing equivalent functionality for the purposes described for the relevant member or element. Terms such as "about" and "substantially", in the context of configuration, relate generally to disposition, location, or configuration that are either exact or sufficiently close to the location, disposition, or configuration of the relevant element to preserve operability of the element within the disclosure which does not materially modify the disclosure. Similarly, unless specifically made clear from its context, numerical values should be construed to include certain tolerances that the person skilled in the art would recognize as having negligible importance as they do not materially change the operability of the disclosure. It will be appreciated that the description and/or drawings identify and describe embodiments of the apparatus (either explicitly or inherently). The apparatus may include any suitable combination and/or permutation of the technical features as identified in the detailed description, as may be required and/or desired to suit a particular technical purpose and/or technical function. It will be appreciated that, where possible and suitable, any one or more of the technical features of the apparatus may be combined with any other one or more of the technical features of the apparatus (in any combination and/or permutation). It will be appreciated that persons skilled in the art would know that the technical features of each embodiment may be deployed (where possible) in other embodiments even if not expressly stated as such above. It will be appreciated that persons skilled in the art would know that other options may be possible for the configuration of the components of the apparatus to adjust to manufacturing requirements and still remain within the scope as described in at least one or more of the claims. This written description provides embodiments, including the best mode, and also enables the person skilled in the art to make and use the embodiments. The patentable scope may be defined by the claims. The written description and/or drawings may help to understand the scope of the claims. It is believed that all the crucial aspects of the disclosed subject matter have been provided in this document. It is understood, for this document, that the word "includes" is equivalent to the word "comprising" in that both words are used to signify an open-ended listing of assemblies, components, parts, etc. The term "comprising", which is synonymous with the terms "including," "containing," or "characterized by," is inclusive or open-ended and does not exclude additional, unrecited elements or method steps. Comprising (comprised of) is an "open" phrase and allows coverage of technologies that employ additional, unrecited elements. When used in a claim, the word "comprising" is the transitory verb (transitional term) that separates the preamble of the claim from the technical features of the disclosure. The foregoing has outlined the non-limiting embodiments (examples). The description is made for particular non-limiting embodiments (examples). It is understood that the non-limiting embodiments are merely illustrative as examples.

What is claimed is:

1. An apparatus for use with an electrocardiogram signal configured to indicate a cardiac cycle of the heart, of a patient, and the heart having the pericardium layer being puncturable by a puncture device, the apparatus comprising:

a computer system being configured to receive the electrocardiogram signal, from an electrocardiographic sensor, configured to indicate the cardiac cycle of the heart; and the computer system also being configured to generate an electrocardiogram tracing based on the electrocardiogram signal that was received; and the computer system also being configured to identify a treatment time duration being configured to span a part of the electrocardiogram tracing that was generated, and the pericardium layer is puncturable during, at least in part, the treatment time duration in such a way that, during, at least in part, the treatment time duration, the blood pressure within the heart urges the pericardium layer to impart a relatively lower amount of tissue force toward the puncture device while the puncture device is positioned proximate to the pericardium layer and, the puncture device is activated to puncture the pericardium layer; and the computer system also being configured to provide the treatment time duration that was identified; and whereby inadvertent damage to the tissue located adjacent to the pericardium layer is reduced while the pericardium layer is punctured during the treatment time duration.

2. The apparatus of claim 1, wherein:

the treatment time duration is configured to span, at least in part, any one of:

isovolumetric contraction as derived from the electrocardiogram tracing; and isovolumetric relaxation as derived from the electrocardiogram tracing; and an RR-interval as derived from the electrocardiogram tracing; and while the patient's blood volume, in the heart, decreases from the patient's left ventricular end-diastolic volume (LVEDV) to the patient's left ventricular end systolic volume (LVESV) as derived from the electrocardiogram tracing; and a ST-T segment as derived from the electrocardiogram tracing; and during the ejection phase of the heart located after a QRS-complex as derived from the electrocardiogram tracing; and an R-wave as derived from the electrocardiogram tracing; and a start of isovolumetric contraction as derived from the electrocardiogram tracing.

3. The apparatus of claim 2, wherein:

a non-optimal time period for puncturing the pericardium layer includes any one of:

a TR-interval as derived from the electrocardiogram tracing; and a TP-interval as derived from the electrocardiogram tracing; and during rapid inflow associated with the diastasis phase and the atrial systole phase of the heart as derived from the electrocardiogram tracing.

4. The apparatus of claim 1, wherein:

the computer system is also configured to provide user-feedback configured to indicate a start time and a stop time of the treatment time duration; and puncturing, of the pericardium layer, starts after a beginning of the treatment time duration; and puncturing, of the pericardium layer, stops before an ending of the treatment time duration.

5. The apparatus of claim 1, wherein:

an energy generator is configured to be in signal communication with the puncture device; and the energy generator includes the computer system.

6. The apparatus of claim 1, wherein:

a pulse generator is configured to be in signal communication with the puncture device; and the pulse generator includes the computer system.

7. The apparatus of claim 1, wherein:

the treatment time duration spans, at least in part, any one of:

isovolumetric contraction as derived from the electrocardiogram tracing; and when the heart is in a state of relative stand-still during isovolumetric contraction as derived from the electrocardiogram tracing.

8. The apparatus of claim 1, wherein:

during the treatment time duration, the pericardium layer is punctured during a time in which the heart is relatively still as derived from the electrocardiogram tracing.

9. The apparatus of claim 1, wherein:

during the treatment time duration, the pericardium layer is punctured during isovolumetric relaxation as derived from the electrocardiogram tracing.

10. The apparatus of claim 1, wherein:

during the treatment time duration, the pericardium layer is punctured starting from any one of:

a beginning of an RR-interval as derived from the electrocardiogram tracing; and while the patient's blood volume decreases from the patient's left ventricular end-diastolic volume (LVEDV) to the patient's left ventricular end systolic volume (LVESV) as derived from the electrocardiogram tracing.

11. The apparatus of claim 1, wherein:

during the treatment time duration, the pericardium layer is punctured starting from any one of:

a ST-T segment as derived from the electrocardiogram tracing; and during the ejection phase located after a QRS-complex as derived from the electrocardiogram tracing.

12. The apparatus of claim 1, wherein:

during the treatment time duration, the pericardium layer is punctured starting from a crest of an R-wave as derived from the electrocardiogram tracing, indicating a start of isovolumetric contraction.

13. The apparatus of claim 1, wherein:

the puncture device includes an energy-emitting puncture device; and the computer system and the energy-emitting puncture device are configured to be in signal communication with each other; and the computer system is also configured to transmit the treatment time duration to the energy-emitting puncture device.

14. The apparatus of claim 13, wherein:

the energy-emitting puncture device is configured to puncture the pericardium layer by selectively emitting energy, to the pericardium layer, during, at least in part, the treatment time duration that was received from the computer system.

15. The apparatus of claim 14, wherein:

the energy-emitting puncture device is configured to stop emission of energy, to the pericardium layer, before an end of the treatment time duration.

16. The apparatus of claim 13, wherein:

the computer system is also configured to transmit an energy-activation signal to the energy-emitting puncture device, in which the energy-activation signal is configured to activate emission of energy from the energy-emitting puncture device so that the energy-emitting puncture device, in use, is urged to selectively emit energy during, at least in part, the treatment time duration.

17. The apparatus of claim 1, wherein:

the puncture device is configured to be in signal communication with the computer system; and the puncture device is configured to receive the electrocardiogram signal.

18. The apparatus of claim 17, wherein:

during the treatment time duration, the pericardium layer is punctured after a crest of the R-wave as derived from the electrocardiogram tracing, which indicates a start of isovolumetric contraction.

19. A method for use with an electrocardiogram signal configured to indicate a cardiac cycle of the heart of a patient, and the heart having the pericardium layer being puncturable by a puncture device, the method comprising:

receiving the electrocardiogram signal, from an electrocardiographic sensor, configured to indicate the cardiac cycle of the heart; and generating an electrocardiogram tracing based on the electrocardiogram signal that was received; and identifying a treatment time duration being configured to span a part of the electrocardiogram tracing that was generated, and the pericardium layer is puncturable during, at least in part, the treatment time duration in such a way that, during, at least in part, the treatment time duration, the blood pressure within the heart urges the pericardium layer to impart a relatively lower amount of tissue force toward the puncture device while the puncture device is positioned proximate to the pericardium layer and, the puncture device is activated to puncture the pericardium layer; and providing the treatment time duration that was identified; and whereby inadvertent damage to the tissue located adjacent to the pericardium layer is reduced while the pericardium layer is punctured during the treatment time duration.

20. A memory assembly being configured to receive and tangibly store an executable program including coded instructions configured to be readable by, and executable by, a computer system, and the executable program is configured to urge a processor to perform predetermined controller operations of the computer system, comprising:

receiving an electrocardiogram signal from an electrocardiographic sensor, and the electrocardiogram signal being configured to indicate a cardiac cycle of the heart; and generating an electrocardiogram tracing based on the electrocardiogram signal that was received; and identifying a treatment time duration being configured to span a part of the electrocardiogram tracing that was generated, and the pericardium layer, of the heart, is puncturable during, at least in part, the treatment time duration in such a way that, during, at least in part, the treatment time duration, the blood pressure within the heart urges the pericardium layer to impart a relatively lower amount of tissue force toward a puncture device while the puncture device is positioned proximate to the pericardium layer and, the puncture device is activated to puncture the pericardium layer; and providing the treatment time duration that was identified; and whereby inadvertent damage to the tissue located adjacent to the pericardium layer is reduced while the pericardium layer is punctured during the treatment time duration.

* * * * *